(12) United States Patent
Kono et al.

(10) Patent No.: US 7,693,251 B2
(45) Date of Patent: Apr. 6, 2010

(54) METHOD AND APPARATUS FOR ULTRASONIC INSPECTION OF REACTOR PRESSURE VESSEL

(75) Inventors: Naoyuki Kono, Mito (JP); Masahiro Miki, Tokai (JP); Yoshio Nonaka, Hitachi (JP); Motoyuki Nakamura, Hitachi (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 290 days.

(21) Appl. No.: 11/834,230

(22) Filed: Aug. 6, 2007

(65) Prior Publication Data

US 2008/0037695 A1   Feb. 14, 2008

(30) Foreign Application Priority Data

Aug. 8, 2006   (JP)  ............................. 2006-215190

(51) Int. Cl.
*G21C 17/10*   (2006.01)
(52) U.S. Cl. ......................................... 376/252; 73/622
(58) Field of Classification Search .................. 73/622; 376/252
See application file for complete search history.

(56) References Cited

U.S. PATENT DOCUMENTS 6,137,853 A * 10/2000 Duckering et al. .......... 376/252

FOREIGN PATENT DOCUMENTS

| JP | 61-270657 | 11/1986 |
| JP | 07-244033 | 9/1995 |
| JP | 09-229916 | 9/1997 |
| JP | 10-026610 | 1/1998 |
| JP | 2005-300224 | 10/2005 |
| JP | 2005-345217 | 12/2005 |

OTHER PUBLICATIONS

"Automated ut Examination of BWR H8 & H9 Core Shroud Welds Using Phased Array Techniques" Hector Diaz, pp. 1-6.

* cited by examiner

*Primary Examiner*—John E Chapman
(74) *Attorney, Agent, or Firm*—Mattingly & Malur, P.C.

(57) ABSTRACT

The ultrasonic probe of the ultrasonic inspection apparatus, which is pushed onto the outer surface of the reactor pressure vessel, transmits and receives an ultrasonic wave to and from a penetration having a welded portion while changing an incident angle of the ultrasonic wave. Based on a result of reception of an echo obtained by the reflection of the ultrasonic wave on the inner surface of the penetration, an inclination angle of the penetration relative to a wall surface of the reactor pressure vessel is measured. A circumferential direction position of the penetration, which corresponds to the inclination angle, is calculated based on the relationship of an inclination angle and a circumferential direction position, which have been calculated in advance. Then, the circumferential direction position can be obtained as information on the inspection position.

10 Claims, 32 Drawing Sheets

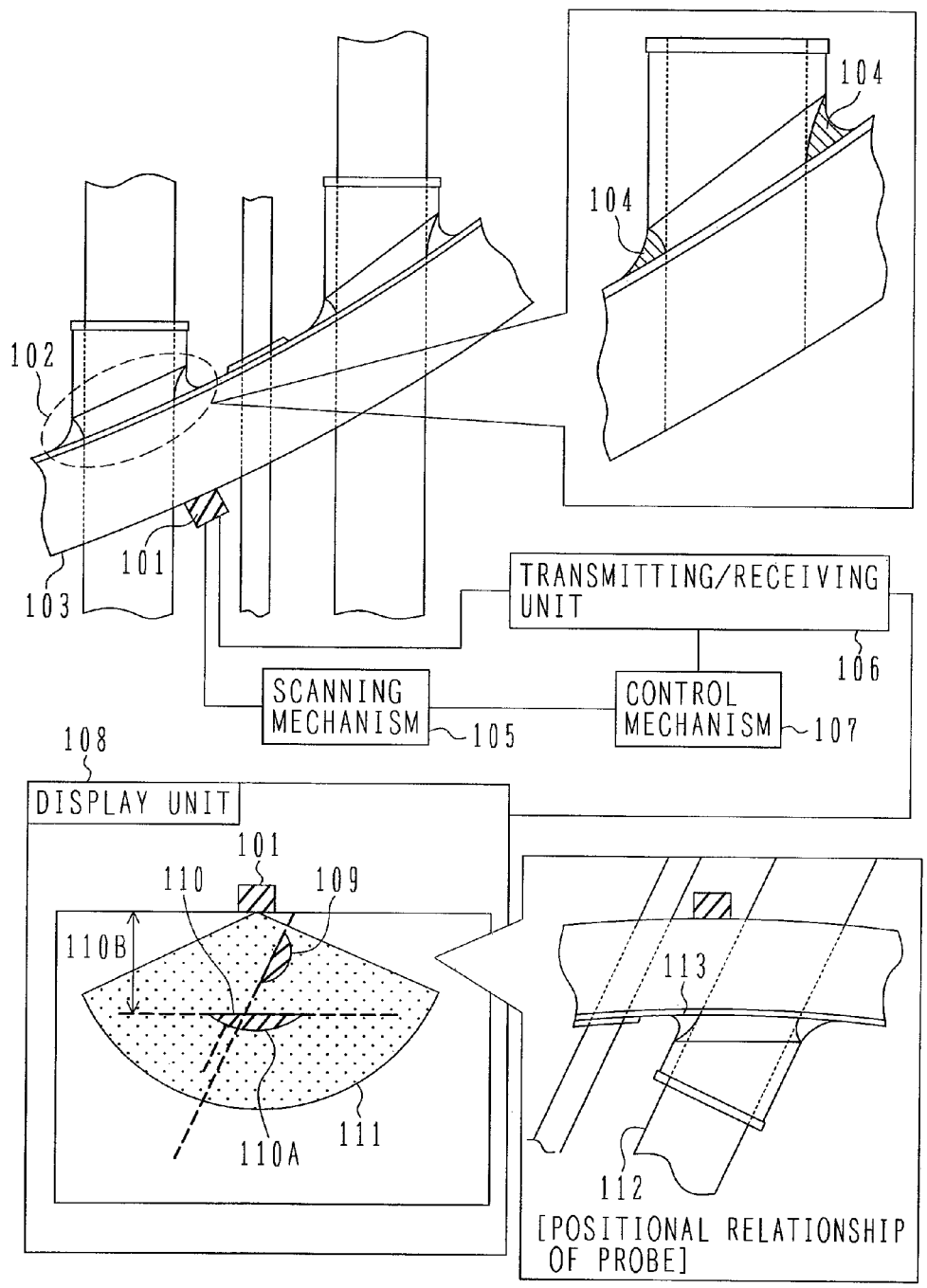

FIG. 2B
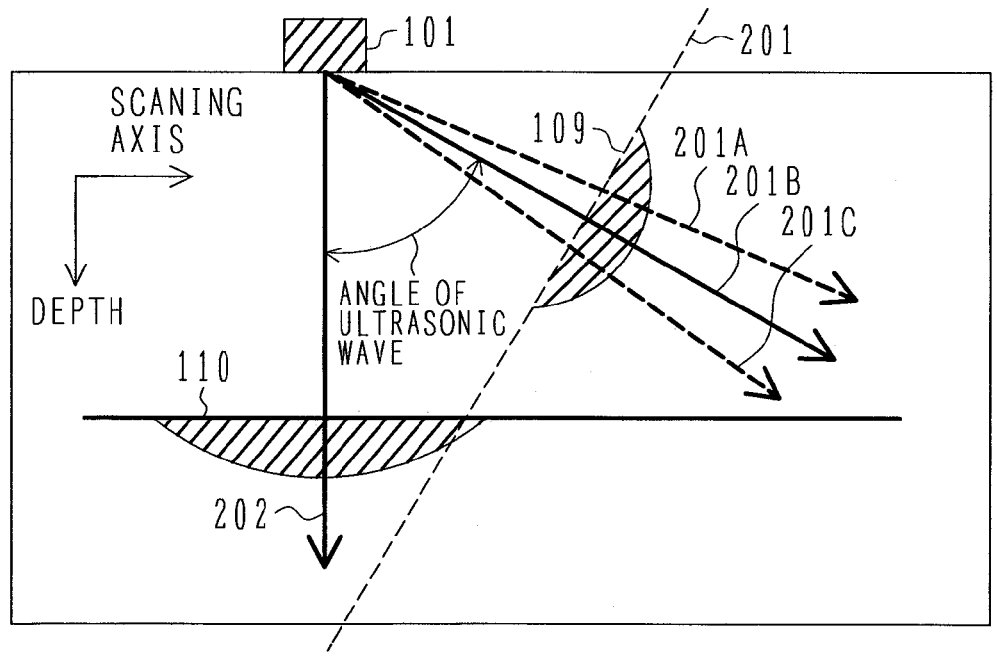
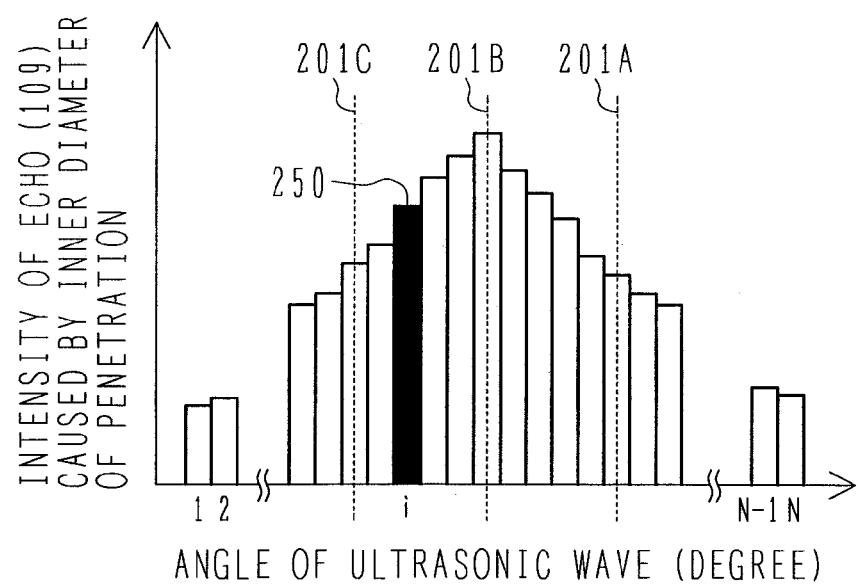

FIG. 5
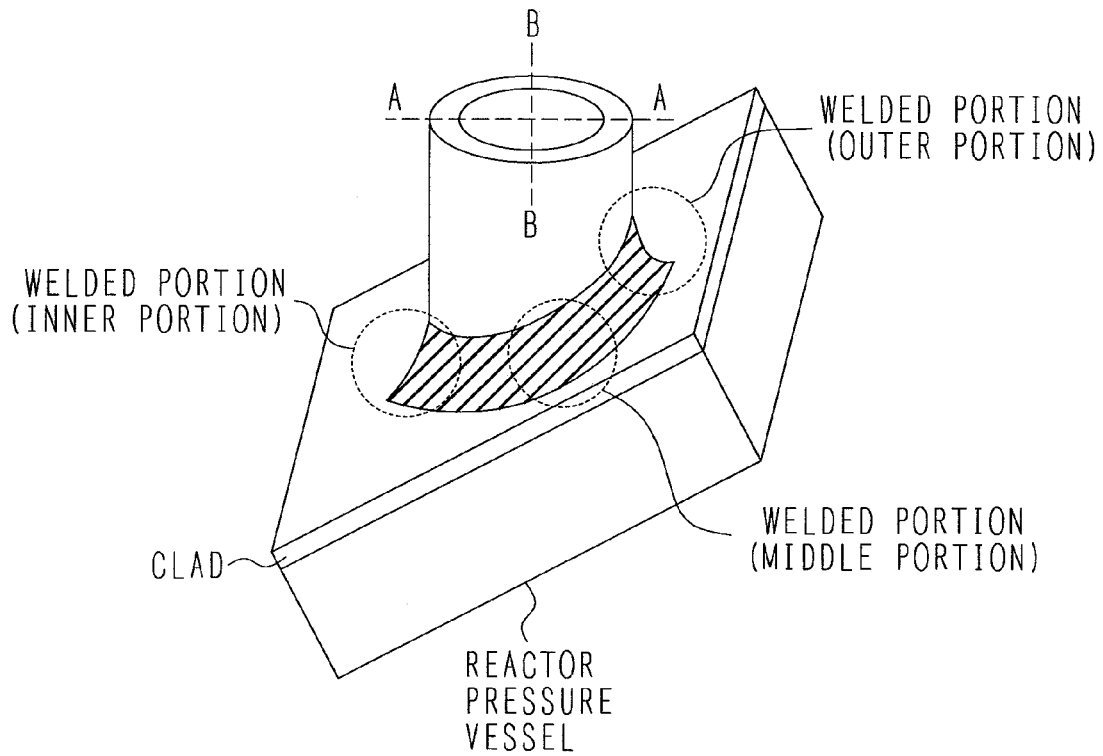
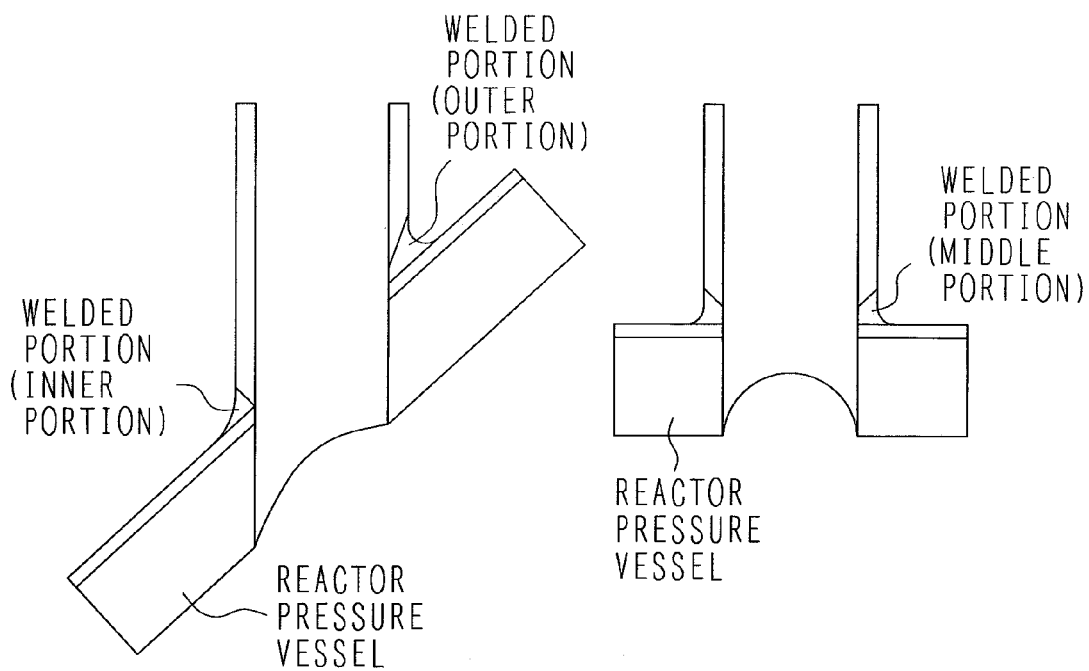

FIG. 7
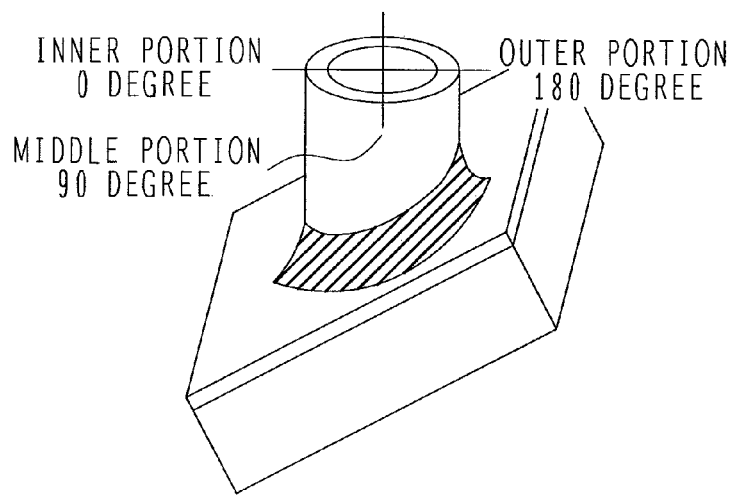
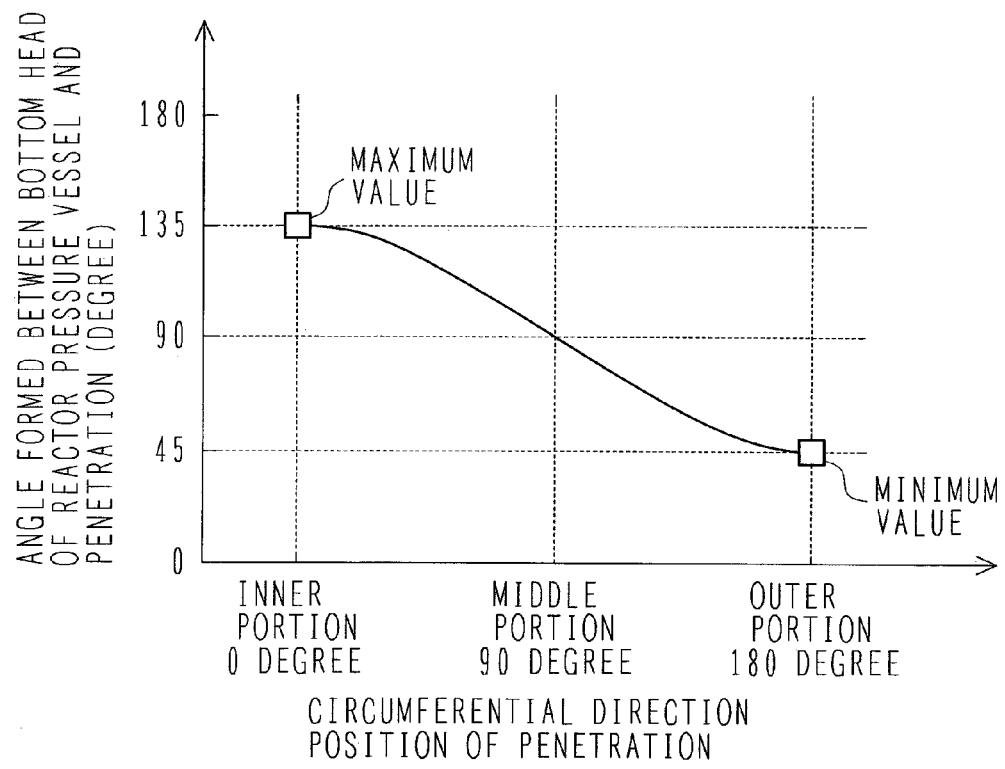

FIG. 8
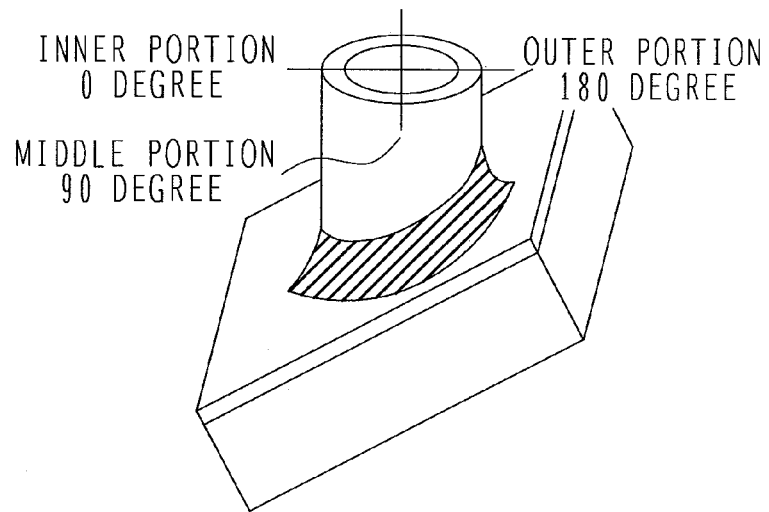
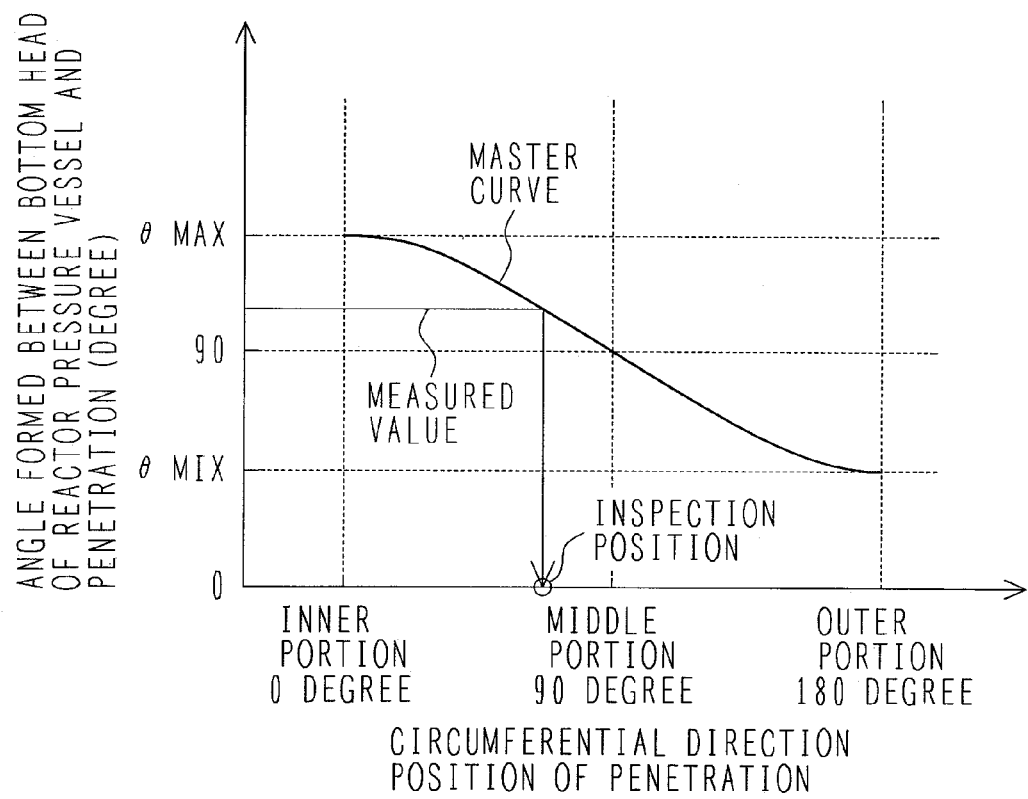

FIG.15A
(A) SCHEMATIC DIAGRAM SHOWING INSPECTION IMAGE
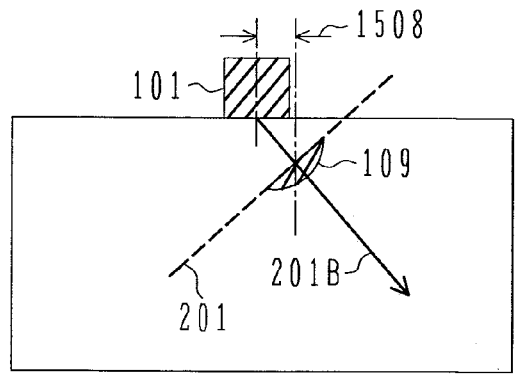
(B) EXAMPLE OF INSPECTION IMAGE (BEFORE SUPERIMPOSITION)
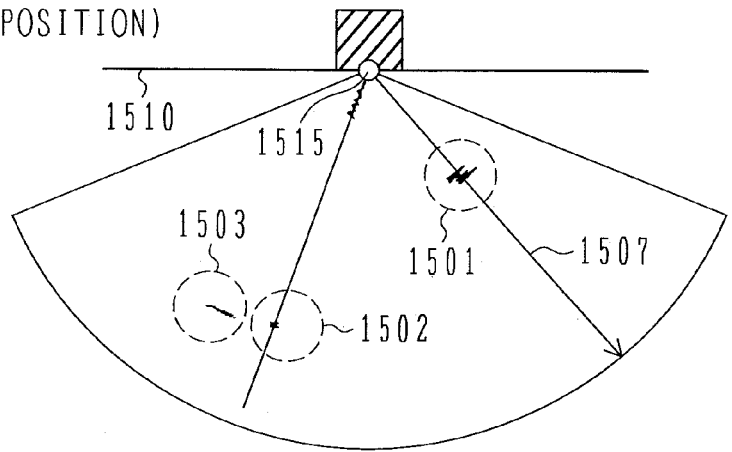
(C) EXAMPLE OF INSPECTION IMAGE (AFTER SUPERIMPOSITION)
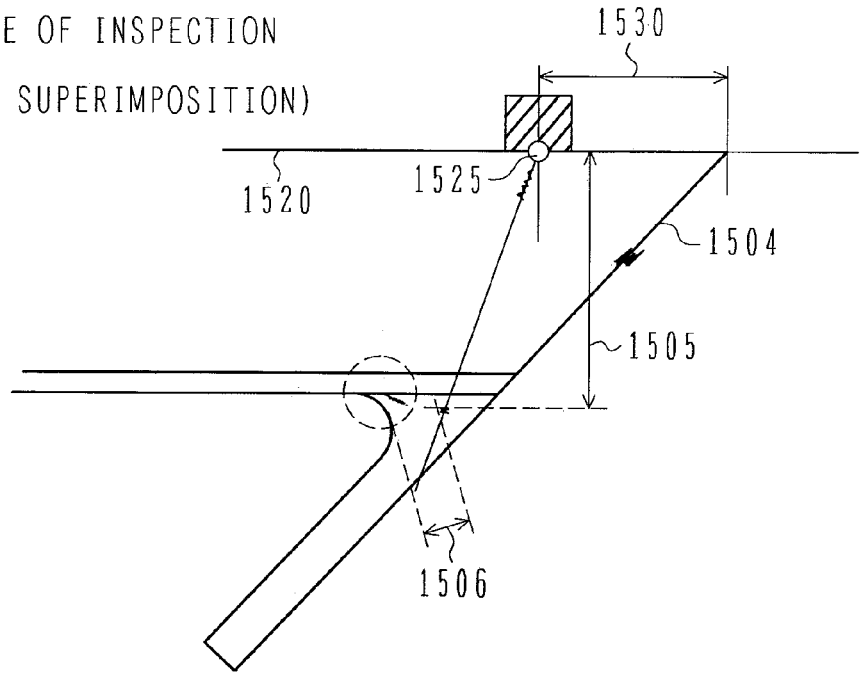

FIG.17
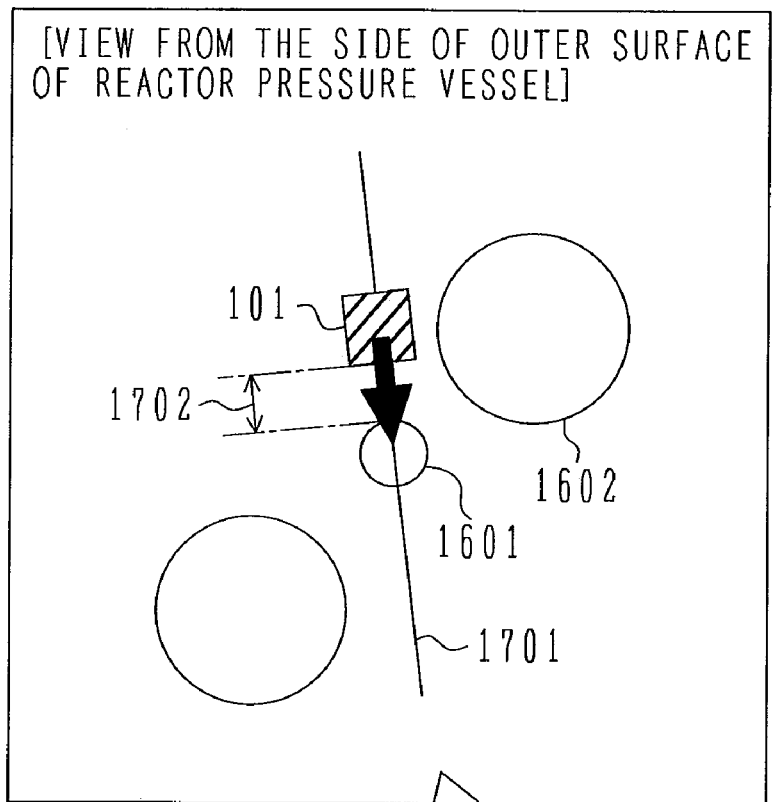
[VIEW FROM THE SIDE OF OUTER SURFACE OF REACTOR PRESSURE VESSEL]
101
1702
1602
1601
1701
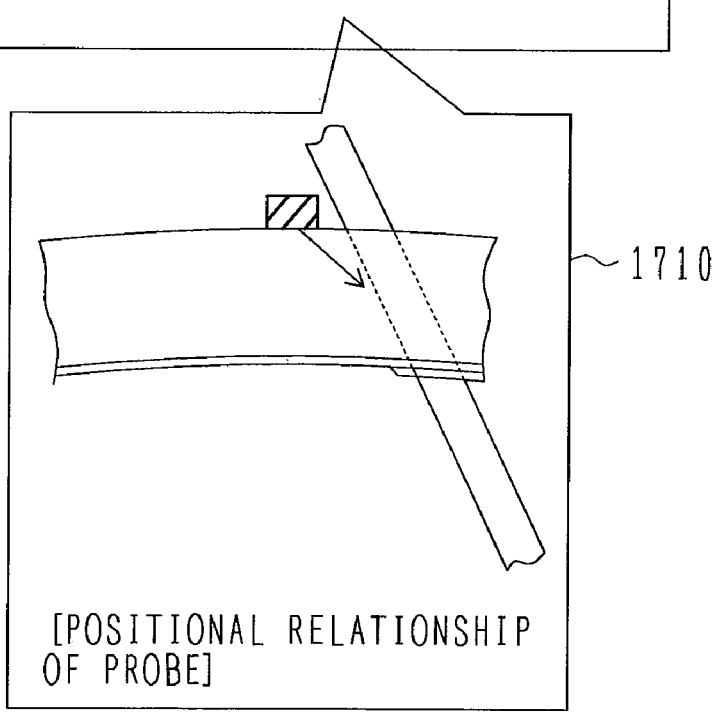
1710
[POSITIONAL RELATIONSHIP OF PROBE]

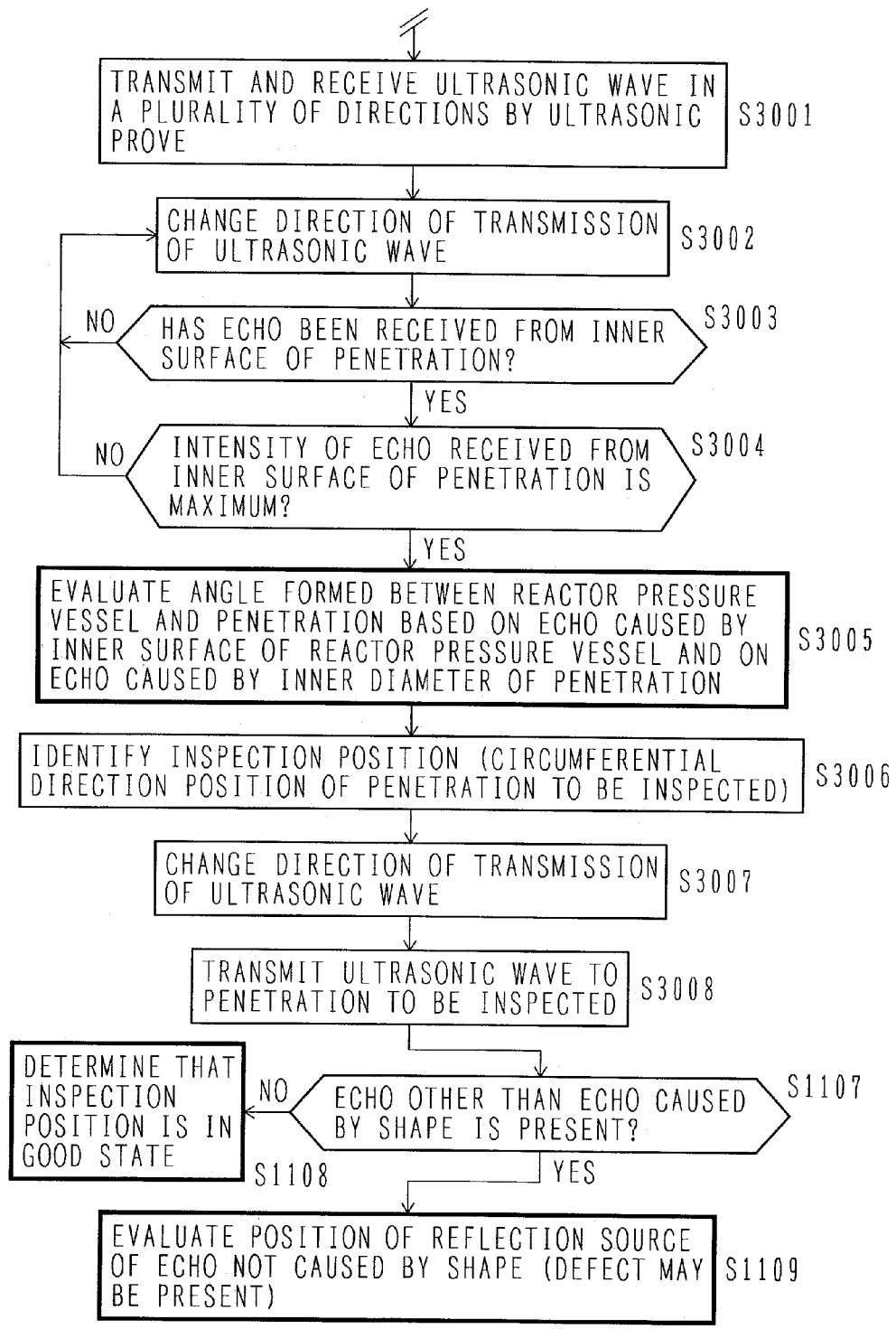

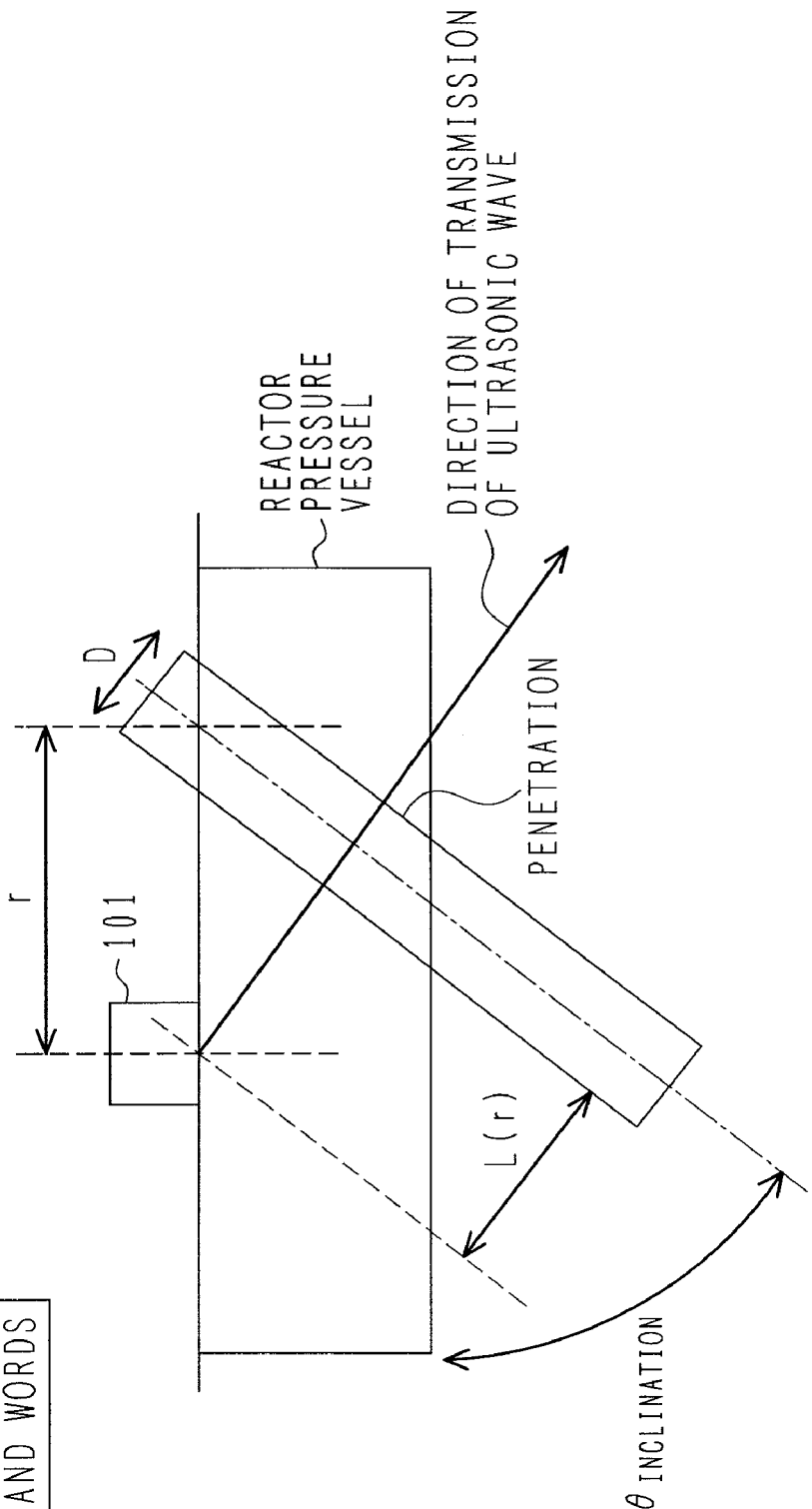

METHOD AND APPARATUS FOR ULTRASONIC INSPECTION OF REACTOR PRESSURE VESSEL

BACKGROUND OF THE INVENTION

1. Field of the Invention

The present invention relates to a technique for an ultrasonic inspection, and more particularly to a technique for an ultrasonic inspection adopted when a penetration of a reactor pressure vessel is a portion to be inspected.

2. Description of the Related Art

As a technique for a nondestructive inspection of a solid material such as metal, inspection techniques using an ultrasonic wave (ultrasonic inspection or ultrasonic flaw detection) have been conventionally used. Known conventional techniques for an ultrasonic inspection of a reactor pressure vessel are described below.

For example, JP-A-07-244033 discloses a technique for an inspection of a welded stub. In the technique, an ultrasonic probe is placed on the inner surface of a penetration (a welded stub of a control rod drive mechanism attached to the bottom head of a reactor pressure vessel) of the reactor pressure vessel, and water is poured into the penetration, so that the inspection is performed with a water soak method.

In addition, JP-A-2005-300224 discloses a technique for an ultrasonic inspection of a penetration (a welded stub of a control rod drive mechanism) of the bottom head of a reactor pressure vessel by using an ultrasonic probe arranged inside the reactor or the reactor pressure vessel.

As described above, for a welded portion of a reactor pressure vessel, it has been common to use a conventional method of an ultrasonic inspection of a penetration of a reactor pressure vessel, the conventional method using an ultrasonic wave which is transmitted through a couplant such as water.

SUMMARY OF THE INVENTION

It can be assumed that a portion of a penetration of a reactor pressure vessel, which is to be inspected by using an ultrasonic wave, is austenite stainless steel or nickel base alloy weld.

The conventional ultrasonic inspection of a penetration of a reactor pressure vessel has been performed so that an ultrasonic probe of an ultrasonic inspection apparatus approaches the periphery of a welded portion (to be inspected) of the penetration. Thus, the conventional ultrasonic inspection allows an ultrasonic wave to be efficiently transmitted to a subject to be inspected.

It is, however, necessary to remotely operate the ultrasonic probe to perform scanning in water when the ultrasonic probe is placed on the inner surface of the penetration of the reactor pressure vessel or the inner surface of the reactor pressure vessel. Therefore, it has been difficult to perform an ultrasonic inspection while ensuring the position of the ultrasonic probe with high accuracy.

In addition, since the surface of a welded portion of a penetration is mechanically processed and finished by using a grinder in many cases, variations such as roughness and undulation are present on the surface of a subject to be inspected. Thus, as described in JP-A-2005-300224, in the technique for performing an ultrasonic inspection from the inside of a reactor pressure vessel, the incident efficiency of an ultrasonic wave to the subject cannot be maintained constant, resulting in variations in signals received by performing the ultrasonic inspection depending on portions to be inspected. Thus, it may be difficult to evaluate a defect through the ultrasonic inspection.

An object of the present invention, therefore, is to ensure the accuracy of the position of an ultrasonic probe in an ultrasonic inspection of a welded portion of a penetration of a reactor pressure vessel, and reduce effects of the surface shape of the welded portion to be inspected.

A method of an ultrasonic inspection according to the present invention is performed as follows. An ultrasonic wave is transmitted to the reactor pressure vessel from the ultrasonic probe of an ultrasonic inspection apparatus and reflected on the penetration of the reactor pressure vessel. The reflected wave is received by the ultrasonic probe. An echo signal based on the reflected wave is displayed on a display unit of the ultrasonic inspection apparatus. The method of the ultrasonic inspection according to the present invention comprises: a first step of calculating an inclination angle of the penetration relative to a wall surface of the reactor pressure vessel based on the result obtained by receiving the reflected wave; and a second step of calculating a circumferential direction position of the penetration having the inclination angle.

The ultrasonic inspection apparatus for inspecting the reactor pressure vessel, according to the present invention, comprises: an ultrasonic inspection device; a scanning mechanism for causing an ultrasonic probe of the ultrasonic inspection apparatus to scan the outer surface of the reactor pressure vessel between penetrations; and means for measuring an inclination angle of the penetration relative to a wall surface of the reactor pressure vessel based on the result obtained by transmitting and receiving an ultrasonic wave by use of the ultrasonic probe.

According to the present invention, in the ultrasonic inspection of the penetration of the reactor pressure vessel, the ultrasonic probe is arranged on the outer surface of the reactor pressure vessel. This ultrasonic inspection is performed while reducing an adverse effect on the ultrasonic inspection of the shape of the surface of a subject to be inspected and identifying the position (hereinafter referred to as a circumferential direction position) of a portion of the penetration, which is inspected at the inclination angle of the penetration relative to the reactor pressure vessel by the ultrasonic inspection apparatus. Therefore, the present invention provides the method and apparatus for the ultrasonic inspection while ensuring accuracy of the position of a portion within an inspection range.

BRIEF DESCRIPTION OF THE DRAWINGS

FIG. 1 is a diagram showing the configuration of an ultrasonic inspection apparatus according to a first embodiment of the present invention.

FIG. 2B is another explanatory diagram showing received waves and the ultrasonic inspection according to the first embodiment.

FIG. 5 is an explanatory diagram showing a penetration that is to be inspected according to embodiments of the present invention.

FIG. 7 is a diagram and a graph showing the relationship between a circumferential direction of the penetration and the angle formed between the reactor pressure vessel and the penetration according to the embodiments of the present invention.

FIG. 8 is a diagram and a graph to explain a master curve according to a second embodiment of the present invention.

FIG. 15A is explanatory diagrams showing an example of a result of the ultrasonic inspection according to the embodiments of the present invention.

FIG. 17 is another diagram showing the third embodiment of the present invention.

FIG. 30 is a flowchart according to the second embodiment of the present invention.

FIG. 31 is a diagram explaining definitions of each symbol and each word used in equation 2.

DESCRIPTION OF REFERENCE NUMERALS

Figure 2A:
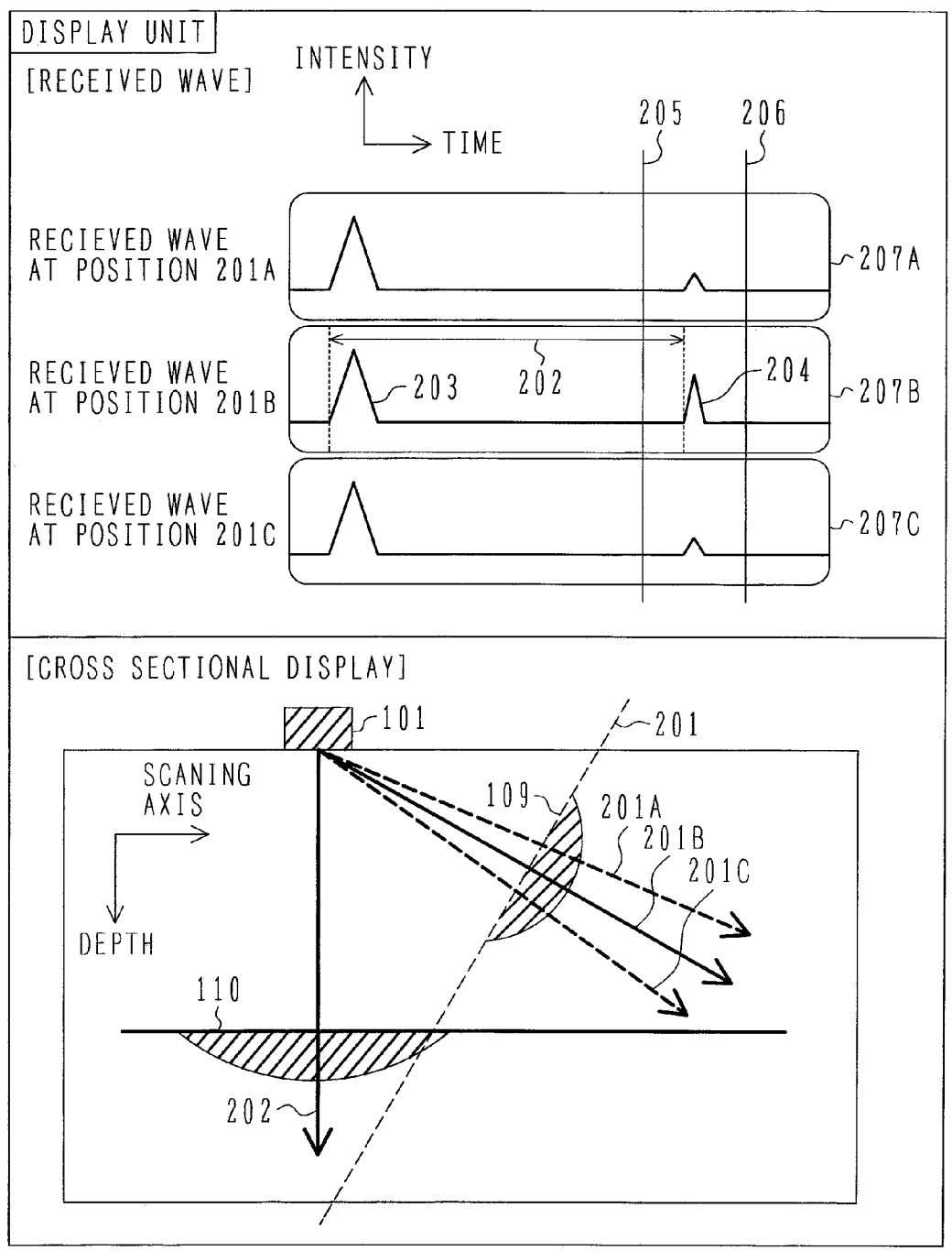
FIG. 2A is an explanatory diagram showing received waves and an ultrasonic inspection according to the first embodiment.

101 . . . Ultrasonic probe
102 . . . Portion to be inspected
103 . . . Reactor pressure vessel
104 . . . Scanning mechanism
105 . . . Transmitting/receiving unit
106 . . . Control unit
107 . . . Display unit
108 . . . Echo caused by inner diameter of penetration

DETAILED DESCRIPTION OF THE PREFERRED EMBODIMENTS

A method of an ultrasonic inspection according to an embodiment of the present invention, which accomplishes the object of the present invention, is performed on a welded portion of a penetration of a reactor pressure vessel as follows. An ultrasonic wave is transmitted from an ultrasonic probe of an ultrasonic inspection apparatus to the penetration and reflected on the penetration. The wave reflected on the penetration is received by the ultrasonic probe. The penetration of the reactor pressure vessel is accordingly inspected based on the reflected wave. The method of the ultrasonic inspection according to the present invention comprises: a step of arranging the ultrasonic probe on the outer surface of the reactor pressure vessel (item (1)); a step of measuring an inclination angle of the penetration relative to a wall surface of the reactor pressure vessel based on an ultrasonic wave transmitted and received by the ultrasonic probe used in the item (1) (item (2)); and a step of evaluating the position of a portion to be inspected based on the measured inclination angle of the penetration (item (3)).

An ultrasonic inspection apparatus according to another embodiment of the present invention inspects a welded portion of a penetration of a reactor pressure vessel as follows. An ultrasonic wave is transmitted from an ultrasonic probe to the penetration and reflected on the penetration. The wave reflected on the penetration is received by the ultrasonic probe. Based on the received wave, the penetration of the reactor pressure vessel is inspected. The ultrasonic inspection apparatus comprises: a ultrasonic wave transmitting/receiving unit for arranging the ultrasonic probe on the outer surface of the reactor pressure vessel (item (4)); and a unit for measuring an inclination angle of the penetration relative to a wall surface of the reactor pressure vessel based on the ultrasonic wave transmitted and received by the ultrasonic wave transmitting/receiving unit (item (5)).

Descriptions will be made of each of the items described above in the case of inspecting the welded portion of the penetration. Incidentally, it is assumed that the reactor pressure vessel, which is to be inspected, is formed of carbon steel (in which the velocity of a longitudinal ultrasonic wave is approximately 5900 m/sec), and that the ultrasonic inspection is performed with an intermediate medium such as water or glycerin (in which the velocity of a longitudinal ultrasonic wave is approximately 1500 m/sec).

Conventionally, it has been required that an ultrasonic probe be arranged on the inner surface of a reactor pressure vessel or on the inner surface of a penetration to be remotely scanned, in terms of the items (1) and (4). However, the reactor pressure vessel is normally arranged in the air. Thus, when the ultrasonic probe is arranged on the outer surface of the reactor pressure vessel, the ultrasonic probe can scan a subject to be inspected with a relatively small distance between the probe and the subject to be inspected. This makes it easy to detect and control the position of the ultrasonic probe.

Taking a boiling water reactor as an example, a reactor pressure vessel has a structure that is called a bottom head. The bottom head is a bottom wall of the reactor pressure vessel. The bottom head is formed into a semicircular shape with a diameter of 6 to 7 meters and has holes (penetrations for control rod drive mechanism) each with a diameter of about 20 cm. The number of the holes is about 100 to 200. Since each of the holes is provided in a vertical direction, the angles formed between the bottom head (having the semicircular shape) of the reactor pressure vessel and the penetrations are different from each other as shown in FIG. 4.

Figure 4:
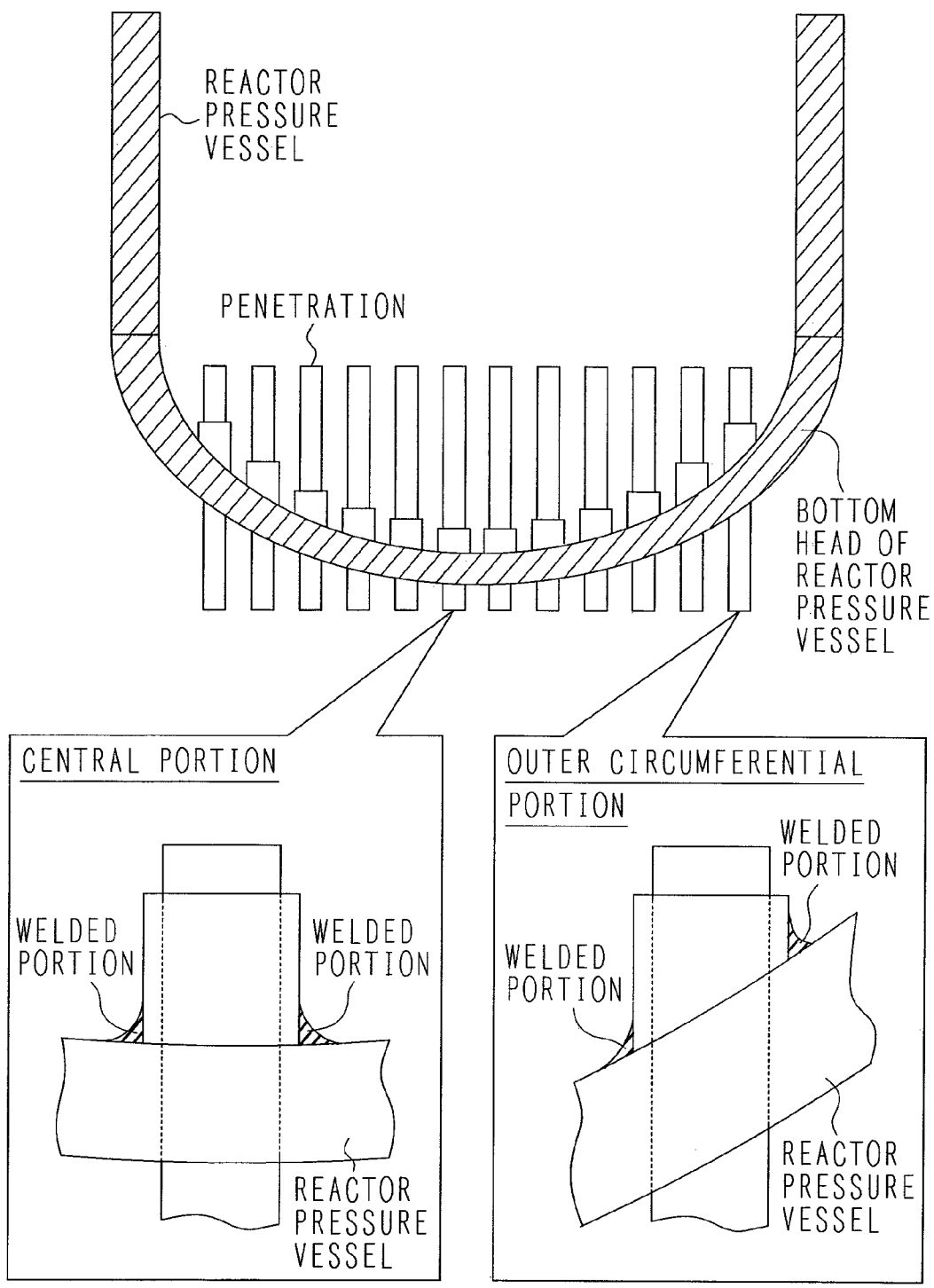
FIG. 4 is an explanatory diagram showing penetrations that are to be inspected according to embodiments of the present invention.

Referring to a schematic diagram shown in FIG. 4, the bottom head of the reactor pressure vessel is substantially orthogonal to the penetrations at a central portion of the bottom head. On the other hand, the angles formed between the bottom head of the reactor pressure vessel and the penetrations are about 45 degrees at the outer circumference of the bottom head.

For a certain penetration, the angle formed between the penetration and the reactor pressure vessel varies depending on the circumferential direction position. FIG. 5 is a diagram schematically showing an example of the penetration placed at the outer circumference. A-A cross section taken along line A-A of FIG. 5 is a cross sectional view in a direction from the central portion of the bottom head of the reactor pressure vessel to the outer circumference of the bottom head. B-B cross section taken along line B-B of FIG. 5 is a cross sectional view in an orthogonal direction to A-A cross section. The angle formed between the penetration and the reactor pressure vessel (bottom head) is approximately 45 degrees at an outer portion, while the angle is approximately 135 degrees at an inner portion on the side opposite to the outer portion. The angle formed between the penetration and a wall of the reactor pressure vessel is approximately 90 degrees at a middle portion as shown in B-B cross section.

Figure 6:
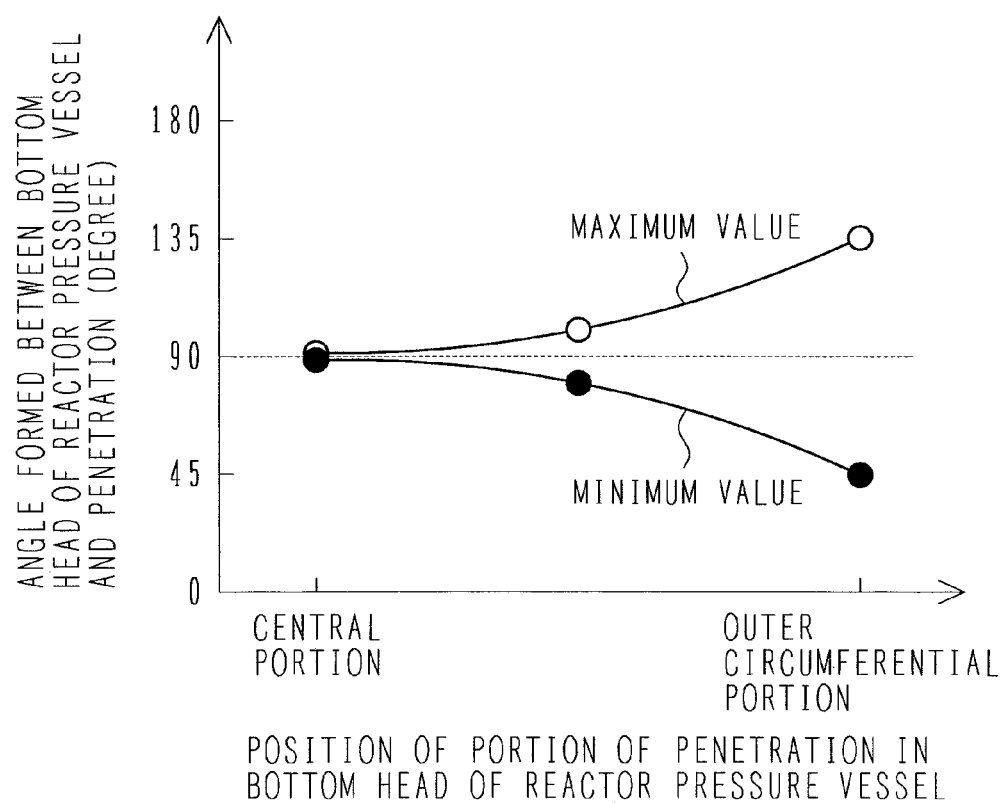
FIG. 6 is a graph showing the relationship between the position of a portion of the penetration to be inspected relative to a bottom head of a reactor pressure vessel and an angle formed between the bottom head of the reactor pressure vessel and the penetration according to the embodiments of the present invention.

As described above, the angle formed between the reactor pressure vessel (bottom head) and the penetration is determined by two factors: the position of a portion (from a central portion to an outer circumferential portion) of the penetration intersecting the bottom head of the reactor pressure vessel; and the position (inner portion, middle portion, outer portion) of a portion of the penetration in the circumferential direction of the bottom head. The positions of the penetrations intersecting the bottom head of the reactor pressure vessel determine minimum and maximum values of the angles formed between the reactor pressure vessel and the penetrations as shown in a graph of FIG. 6. As shown in FIG. 7, the positions of portions of the penetration in the circumferential direction of the bottom head determine the minimum and maximum values of the angles formed between the reactor pressure vessel and the penetrations.

Similarly to the items (2) and (5) described above, the ultrasonic probe arranged on the outer surface of the reactor pressure vessel transmits and receives an ultrasonic wave in an oblique direction so that the inclination angle formed between the penetration and the reactor pressure vessel (bottom head) can be measured. The ultrasonic wave transmitted/received to/from a target to be inspected at an angle of 90 degrees relative to the target is reflected with an energy efficiency of approximately 100 percent. This property of the ultrasonic wave is used in the abovementioned measurement. In the case where the ultrasonic wave is transmitted/received to/from the surface of the inclined penetration at an angle of 90 degrees relative to the surface, the intensity of a signal received is the highest. Thus, the inclination angle of the penetration can be evaluated.

Like the item (3), the inclination angle of the penetration relative to reactor pressure vessel, or the angle formed between the bottom head of the reactor pressure vessel and the penetration can be measured to evaluate the position of a portion of the penetration in the circumferential direction, the portion being under inspection. As shown in an example of FIG. 7, since the circumferential position of a portion of the penetration and the inclination angle of the penetration are in a one-to-one relationship, the position of the portion of the penetration can be estimated based on the inclination angle that has been measured.

The display unit of the ultrasonic inspection apparatus may display the measured inclination angle, or the angle formed between bottom head of the reactor pressure vessel and the penetration.

For the ultrasonic inspection described in the items (4) and (5), a unit described in the following item (6) may be used. The ultrasonic inspection apparatus having functions corresponding to the items (4) and (5) preferably includes the unit for storing the inclination angle of the penetration (item (6)).

Using the item (6), the ultrasonic inspection apparatus stores a design drawing and a master curve (as shown in FIG. 8) indicating the angle (inclination angle) formed between a wall surface of the bottom head of the reactor pressure vessel and the penetration. Thus, based on the inclination angle measured by using the items (2) and (5), it is possible to specify a position that is under inspection, or the position of a portion of the penetration in the circumferential direction.

The method and apparatus for the ultrasonic inspection will be described in detail with reference to embodiments shown in the accompanying drawings.

First Embodiment

FIG. 1 is a diagram showing a first embodiment of the present invention. In FIG. 1, an inspection target 102 (shown in a circle indicated by a broken line) is inspected by pushing an ultrasonic probe 101 of the ultrasonic inspection apparatus toward the outer surface of a reactor pressure vessel 103. The ultrasonic probe 101 receives an ultrasonic wave through the reactor pressure vessel 103. Details of the inspection target 102 are shown as a welded portion 104 (shaded portion) in an enlarged view of FIG. 1. The welded portion 104, which is to be inspected, has a surface with a curvature. In addition, the welded portion 104 has a ring shape surrounding the penetration.

A key feature of the present embodiment is the welded portion 104 surrounding the penetration of the reactor pressure vessel 103. In the case of a boiling water reactor (BWR), a stub tube weld of a control rod drive (CRD) mechanism, an incore monitor (ICM) housing weld, and the like are to be inspected. In the case of a pressurized water reactor (PWR), a weld of a penetration of a reactor pressure vessel lid and the like are to be inspected.

Since FIG. 1 shows the boiled water reactor, the ultrasonic probe is placed on the outer surface of the bottom head of the reactor pressure vessel. In the case of the pressurized water reactor, the ultrasonic probe is placed on the outer surface of the upper lid of the reactor pressure vessel. Although the positions of the ultrasonic probe and the reactor pressure vessel shown in FIG. 1 are vertically inversed, this can be also applied to the present invention.

Figure 22:
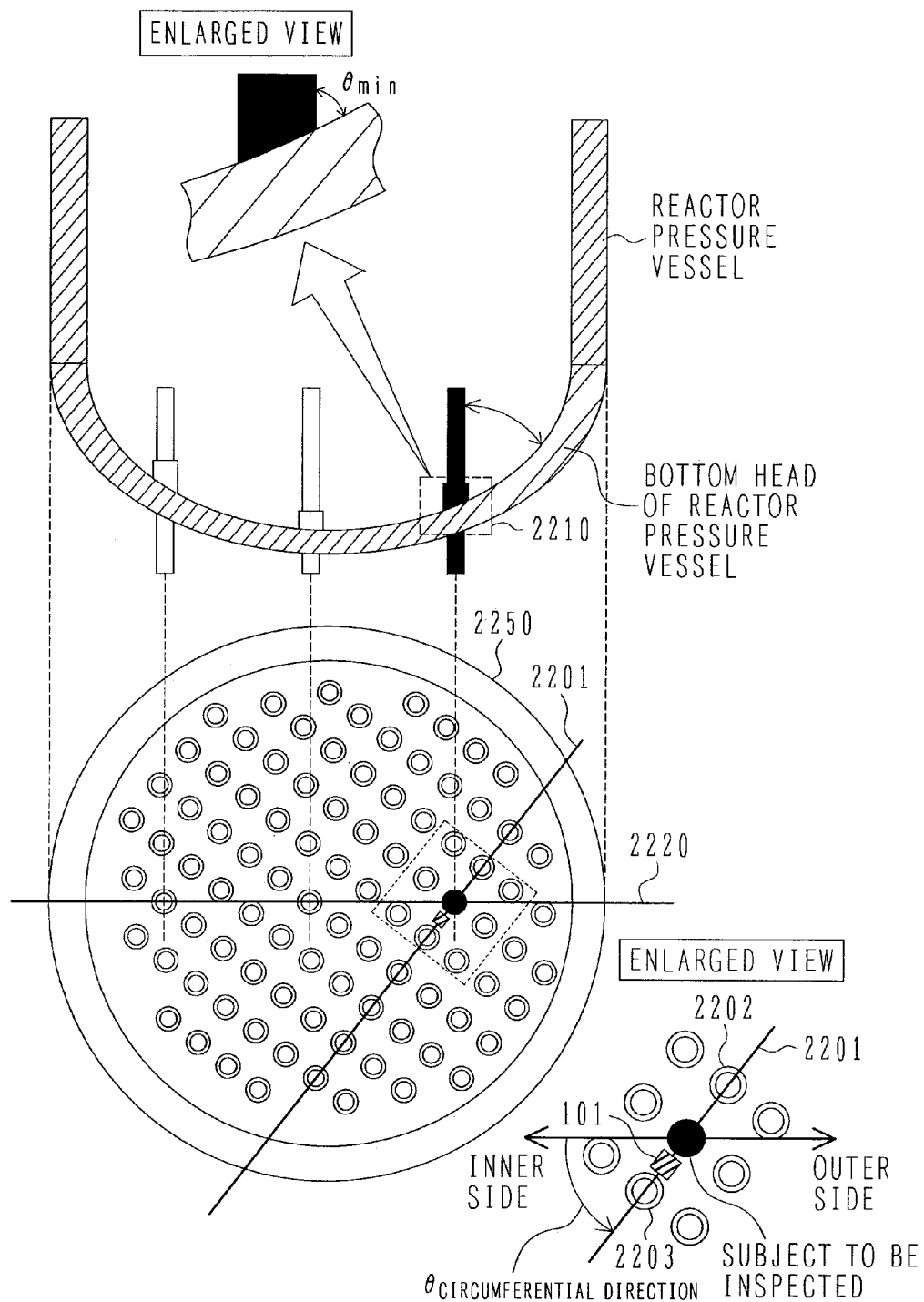
FIG. 22 is another diagram explaining the first embodiment of the present invention.
Figure 24:
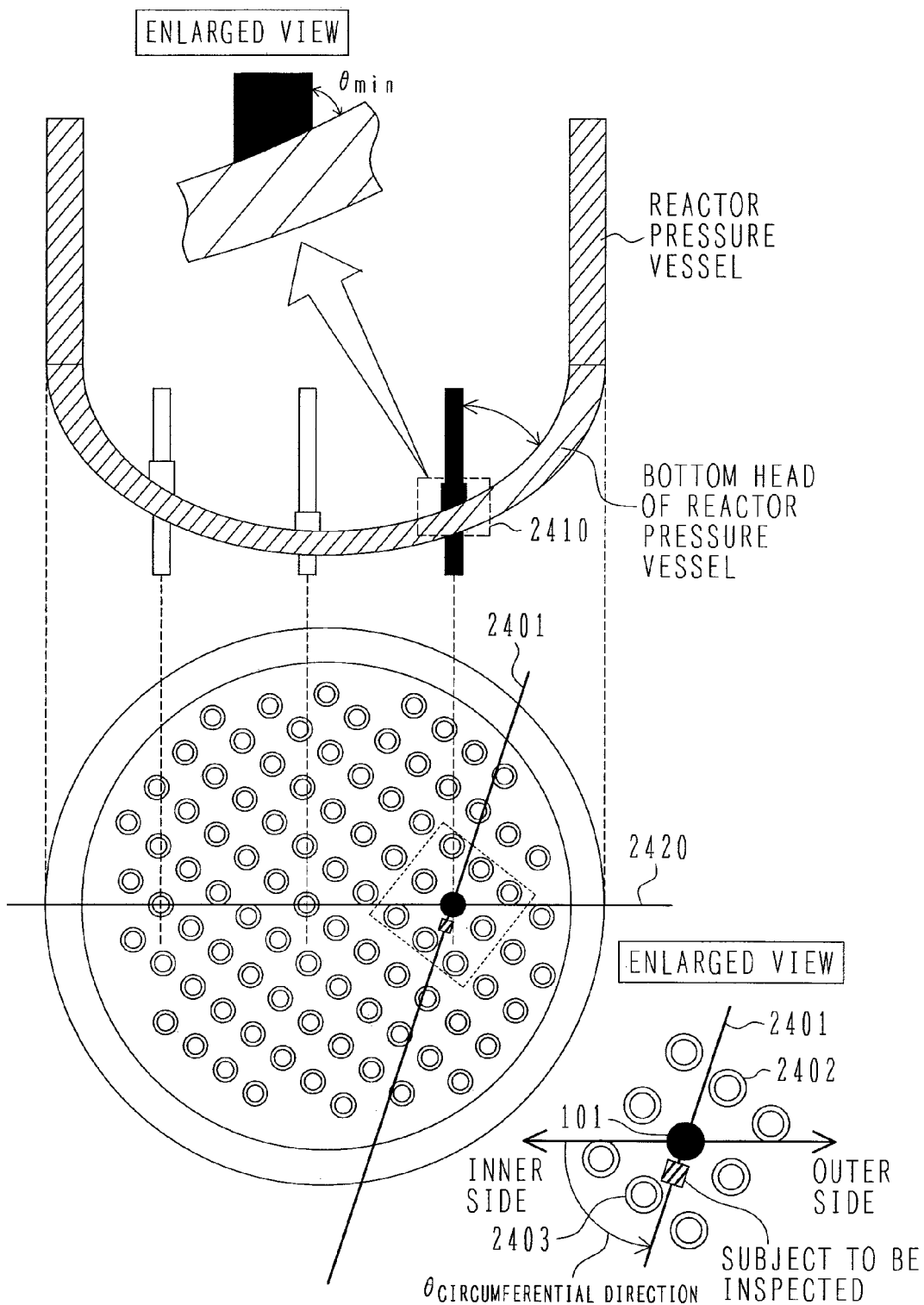
FIG. 24 is another diagram explaining the third embodiment of the present invention.

A description will be made of the relationship of the inspection target 102 (corresponding to an inspection target 2210 shown in FIG. 22) and penetrations in the vicinity of the inspection target 102 with reference to FIGS. 22 and 24. Based on the bottom head of the reactor pressure vessel provided in the boiled water reactor as shown in the schematic diagram of FIG. 4, a geometric relationship of an inspection target 2210 and penetrations in the vicinity of the inspection target 2210 includes the following: the case where a cross section of a line 2201 running on the centers of the ultrasonic probe 101 and the inspection target 102 passes the centers of neighboring penetrations (2202 and 2203) as shown in FIG. 22; and the case where a cross section of a line 2401 running on the centers of the ultrasonic probe 101 and the inspection target 102 does not pass the centers of neighboring penetrations (2402 and 2403) as shown in FIG. 24. The latter case shown in FIG. 24 is more general than the former case shown in FIG. 22. In the first embodiment and a second embodiment, the former case shown in FIG. 22 will be described for simplicity. The case shown in FIG. 24 will be described in a third embodiment to provide differences between the two cases.

It is assumed that, in order to efficiently transmit an ultrasonic wave to the inspection target 102, a contact medium (also called couplant) such as water or glycerin, which is used as an intermediate medium, is coated or filled between the ultrasonic probe 101 and the reactor pressure vessel 103 on which the ultrasonic probe 101 is placed.

The ultrasonic probe 101 is connected to a transmitting/receiving unit 106. The transmitting/receiving unit 106 has a function for transmitting a pulser voltage used to transmit an ultrasonic wave to the ultrasonic probe 101. The transmitting/receiving unit 106 also has a function for receiving a signal that has been received by the ultrasonic probe 101.

The ultrasonic probe 101 is one- or two-dimensionally scanned on the outer surface of the reactor pressure vessel 103 by a scanning mechanism 105. A range to be scanned or a position to be scanned (i.e., the position of the ultrasonic probe 101) by the scanning mechanism 105 is controlled by a control mechanism 107. Among them, at least information on the position to be scanned is transmitted to the transmitting/receiving unit 106. The position to be scanned (the position of the ultrasonic probe 101) and a signal received at the position are combined and stored.

Figure 9:
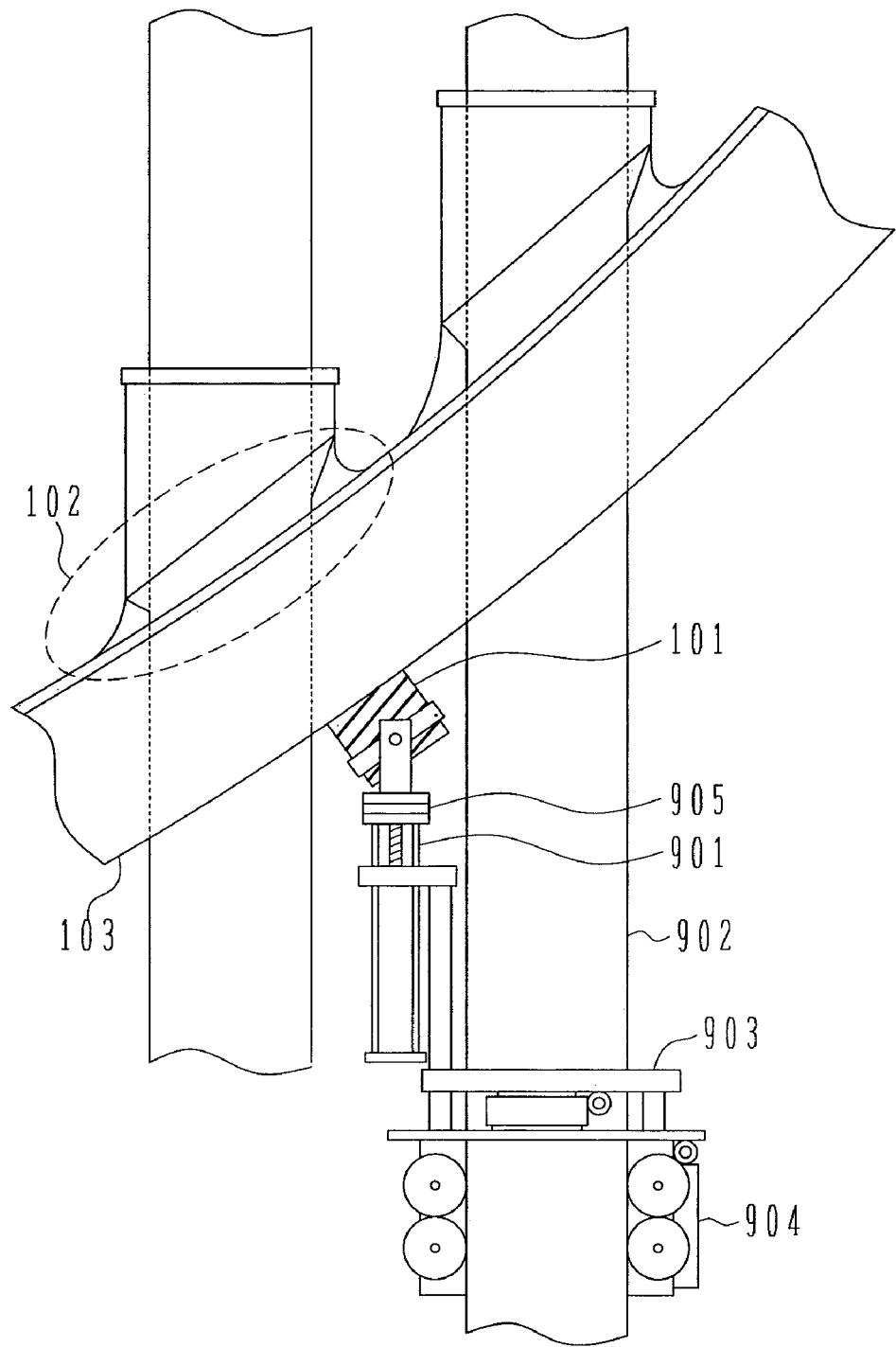
FIG. 9 is a diagram showing an example of the configuration of a scanning mechanism for scanning the outer surface of the reactor pressure vessel according to the embodiment of the present invention.

FIG. 9 is a diagram showing an example of the structure of the scanning mechanism 105. The scanning mechanism 105 has a pushing mechanism 901 for pushing the ultrasonic probe 101 to bring the ultrasonic probe 101 into contact with the outer surface of the reactor pressure vessel 103. To move the pushing mechanism 901 to a predetermined portion to be inspected, the following, for example, are provided: a rotation mechanism 903 for guiding a control bar guiding tube 902 (hereinafter merely also referred to as a tube); a vertical movement mechanism 904; and a probe rotation mechanism 905 for directing the ultrasonic probe to a predetermined direction. The scanning mechanism 105 makes it possible to push and place the ultrasonic probe 101 onto and on the outer surface of the reactor pressure vessel 103 for a predetermined penetration which is to be inspected among the penetrations of the reactor pressure vessel 103.

The signal, which has been received by the transmitting/receiving unit 106 and stored together with the information on the position of the ultrasonic probe 101, is displayed on the display unit 108 as a wave form or an image. A description below will be made of the case where an array probe is used as the ultrasonic probe to perform an inspection with a phased array technique.

Figure 10:
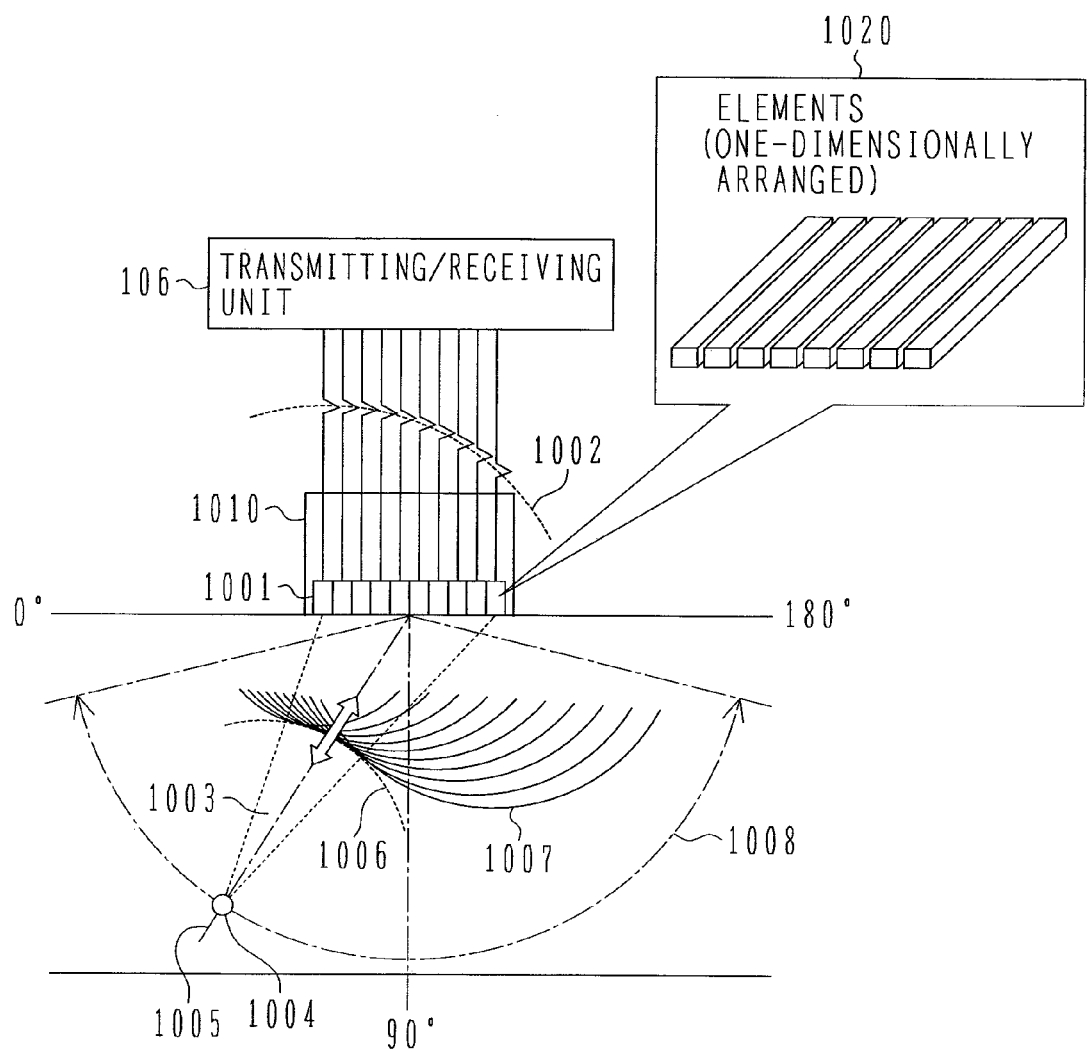
FIG. 10 is a diagram explaining an array probe and a phased array technique according to the embodiment of the present invention.

The phased array technique using the array probe will be described below with reference to FIG. 10. In FIG. 10, reference numeral 1010 is an array probe. The array probe 1010 typically has several to several ten small transducers (elements) 1001 regularly arranged. A linear array probe (shown with reference numeral 1020 in FIG. 10) is well known as such an array, which has rectangular elements arranged in one direction. Although the size of the element is slightly varied depending on a frequency, the variation is about several tenth to several millimeters. The phased array technique is to vary the timing of transmission (oscillation) and reception performed at the elements so as to combine various ultrasonic beams.

When the phased array technique is used, a pattern 1002 (delay time pattern) of the timing is set in the elements 1001 forming an array sensor 1010. Wavefronts 1007 generated from each of the elements 1001 are combined to be a combined wavefront 1006 that propagates in a direction 1005. The combined wavefront 1006 is reinforced with another combined wavefront at a point 1004, which is called a focal point. A distribution of ultrasonic waves generated by the array probe 1010 is finally shaped like an ultrasonic beam 1003 that is focused on the focal point 1004. A feature of the phased array technique is to vary the delay time pattern 1002 so as to electronically control the depth of the focal point 1004 and the propagation direction 1005 at high speed.

Figure 20:
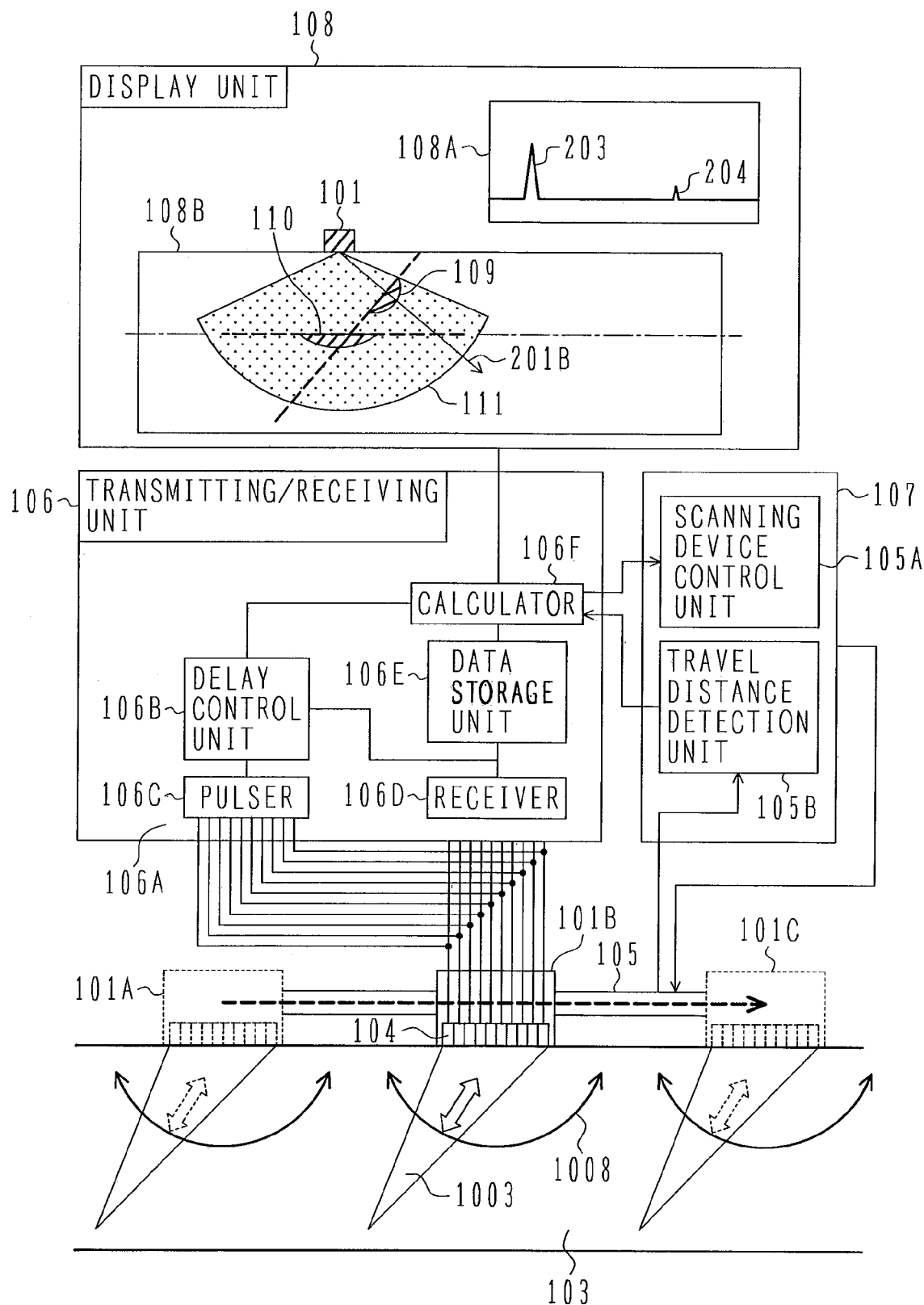
FIG. 20 is a diagram showing an ultrasonic inspection apparatus according to the present invention.

Next, the ultrasonic inspection apparatus will be described in detail with reference to FIG. 20. The configuration of the ultrasonic inspection apparatus having the ultrasonic probe 101 that is an array probe, transmitting/receiving unit 106, control mechanism 107, and display unit 108 will be described as an example. The transmitting/receiving unit 106 has a delay control unit 106B, a pulser 106C, a receiver 106D, a data storage unit 106E, a calculator 106F, and a case 106A for storing them.

In the case of using the phased array technique, pulse signals are supplied to each of elements forming the ultrasonic probe 101 at different timings from each other as described above. By supplying the pulse signals in the above manner, the propagation direction and the focal point of the ultrasonic beams can be electrically controlled. The pattern of the timing (delay time pattern) is calculated by the calculator 106F. In this case, parameters necessary for the calculation, such as an incident angle of the ultrasonic wave, refraction angle of the ultrasonic wave, presence of the focal point, position of the focal point, and depth of the focal point, are entered into the calculator 106F by a user using a pointing device or a keyboard. In accordance with the delay time pattern set for each of the elements, a trigger signal that has been shifted by a time corresponding to the delay time is generated from the delay control unit 106B and transmitted to the pulser 106C that provides a high voltage pulse to each of the elements forming the array probe. Since the pulser 106C is connected to each of the elements forming the array probe, the ultrasonic probe 101, which is an array probe, generates an ultrasonic beam 1003 in the reactor pressure vessel 103 to be inspected. The ultrasonic beam 1003 proceeds to a focal point in a certain direction. The focal point and the direction are defined by the delay time pattern. If a reflection source is present in or on a subject to be inspected, a reflected ultrasonic wave re-propagates in the reactor pressure vessel 103 and reaches the ultrasonic probe 101.

In this case, since the ultrasonic probe 101 is an array probe, the scanning mechanism 105 as shown in FIG. 9 is used to move the ultrasonic probe 101 on the outer surface of the reactor pressure vessel 103 so that an ultrasonic inspection is performed on a wide region to be inspected. The scanning mechanism 105 is composed of a scanning device control unit 105A and a travel distance detection unit 105B. The scanning device control unit 105A controls movement of a scanning device 105, and the travel distance detection unit 105B detects the position of the ultrasonic probe 101. A motor may be used as the scanning device control unit 105A and a motor drive. An encoder may be used as the travel distance detection unit 105B.

The ultrasonic wave that has reached the ultrasonic probe 101 is piezoelectrically converted to an electric signal by each of the elements of the ultrasonic probe 101. The converted electric signal is transmitted to the receiver 106D that is connected to each of the elements. Since the electric signal transmitted from each of the elements is very feeble in many cases, it is amplified to a several voltage by an amplifier. After that, the amplified electric signal is converted to a digital signal. The digital signal that has been received is stored in a data storage unit 106E as digital data corresponding to the position of the ultrasonic probe 101, which is positioned by the scanning mechanism 105.

The transmitting/receiving unit 106 transmits information on the delay time pattern 1002 to the ultrasonic probe 101. After receiving the information, the ultrasonic probe 101 transmits or receives ultrasonic waves while varying the propagation direction 1005 so that the ultrasonic waves are formed into, for example, a fan shape 111. When the positional relationship between the inner surface of the reactor pressure vessel 103, the inner diameter 112 of the penetration and the ultrasonic probe 101 is provided as shown in "positional relationship of probe" of FIG. 1, two types of signals are mainly received by the ultrasonic probe 101. A first echo 109 is a wave reflected from the inner diameter 112 of the penetration. A second echo 110 is a wave reflected from the inner surface 113 of the reactor pressure vessel 103. Based on the two types of the echoes, the state (e.g., presence of a defect, size of the defect) of a portion (to be inspected) of the penetration is evaluated.

Figure 11:
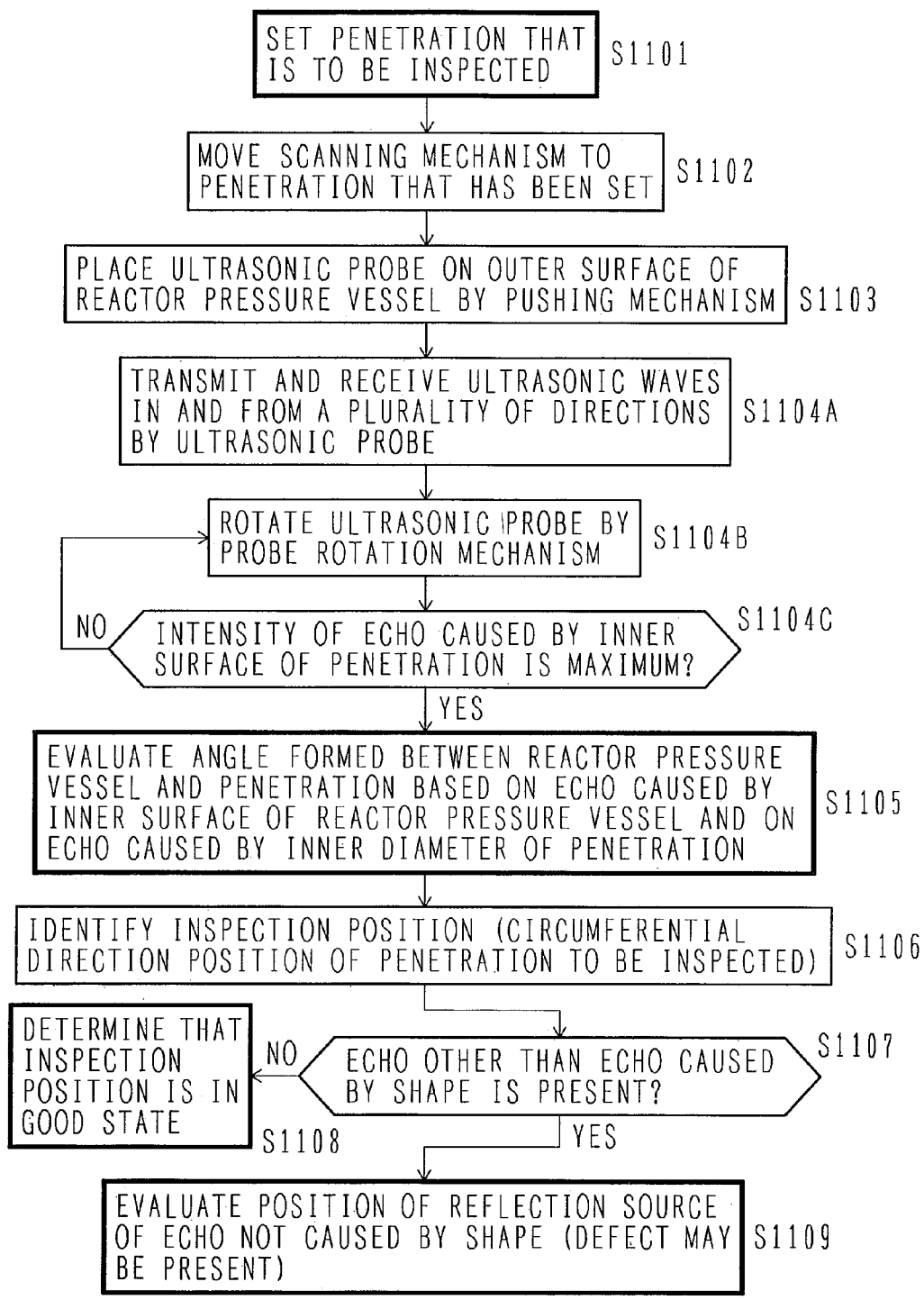
FIG. 11 is a flowchart according to the first embodiment of the present invention.

FIG. 11 is a flow chart of the ultrasonic inspection according to the present embodiment. To perform the ultrasonic inspection, a penetration to be inspected is set in step S1101 when a plurality of penetrations are present. Next, the scanning mechanism moves until the penetration to be inspected can be inspected in step S1102. Then, the pushing mechanism 901 pushes the ultrasonic probe 101 toward the outer surface of the reactor pressure vessel 103 in step S1103.

The ultrasonic probe 101 that has been pushed toward the outer surface of the reactor pressure vessel 103 transmits ultrasonic waves in a plurality of directions in step S1104. When the reflection source is present, an echo (reflected wave) is received from an angular direction in which the reflection source is present. Since the array probe 1010 is used as the ultrasonic probe 101, ultrasonic waves present in the fan shape 111 are transmitted and received. An image obtained based on the ultrasonic waves is displayed on the display unit 108.

Main signals received by the ultrasonic probe 101 includes the echo 110 obtained by transmitting/receiving an ultrasonic wave in a vertical direction to/from the inner surface of the reactor pressure vessel 103 and the echo 109 obtained from the inner surface of the penetration.

Figure 21A:
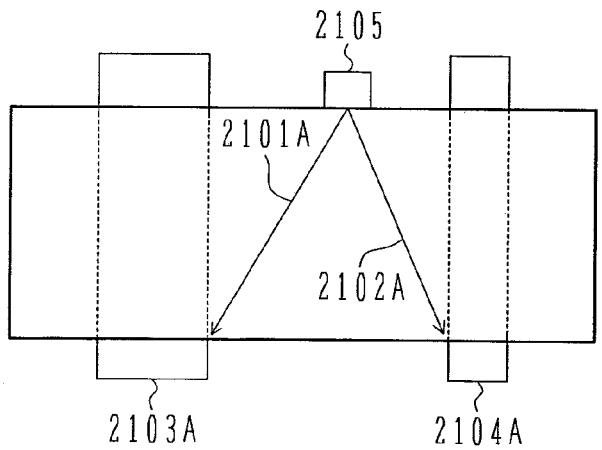
FIG. 21A is a diagram explaining the first embodiment of the present invention.
Figure 21B:
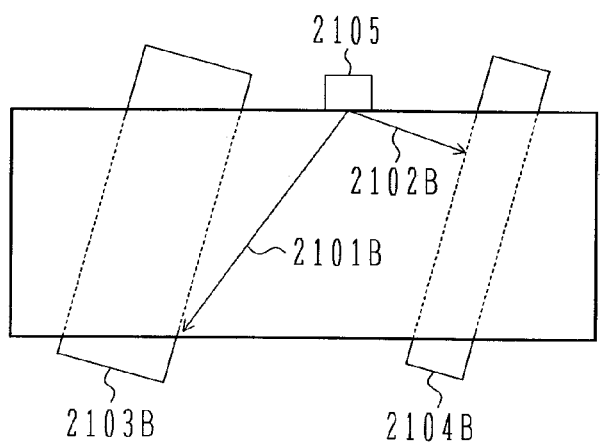
FIG. 21B is another diagram explaining the first embodiment of the present invention.
Figure 21C:
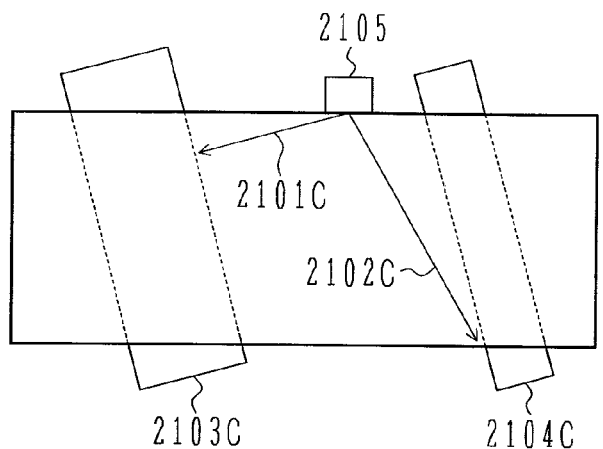
FIG. 21C is another diagram explaining the first embodiment of the present invention.

With reference to FIGS. 21A to 21C, types of echoes obtained from the inner surface of the penetration will be described below. In FIGS. 21A to 21C, reference numerals 2103A, 2103B, 2103C each denote a penetration to be inspected. Based on the angle θ formed between the reactor pressure vessel and the penetration, the echoes obtained from the inner surface of the penetration can be divided into three types. Firstly, when the reactor pressure vessel is substantially orthogonal to the penetration (see FIG. 21A), a reflected echo can be received by transmitting an ultrasonic wave 2101A from an ultrasonic probe 2105 (which is the same as the ultrasonic probe 101) to a region in which the inner surfaces of the penetration and the reactor pressure vessel intersect each other. Similarly, a reflected echo can be received by transmitting an ultrasonic wave 2102A from the ultrasonic probe 2105 to a region in which the inner surface of the reactor pressure vessel intersects the inner surface of a penetration 2104A adjacent to the penetration 2103A to be inspected. In this case, an angular range which can be regarded as substantially the right angle is limited to a range approximately from 70 to 110 degrees when it is assumed that the echoes with a certain intensity can be received by transmitting the ultrasonic waves 2101A and 2102A.

Secondary, in the case where the reactor pressure vessel and the penetration are arranged with a certain angle (e.g., 20 degrees or more) formed between them, an ultrasonic wave 2101B is transmitted from the ultrasonic probe 2105 to a region in which the inner surfaces of the reactor pressure vessel and the penetration intersect each other with an acute angle (see FIG. 21B). In this case, similarly to the case of FIG. 21A, it is expected that a reflected echo is received from the region in which the inner surfaces of the reactor pressure vessel and the penetration intersect each other with the acute angle. The intensity of the reflected echo, however, may be insufficient when it is received. Thus, it may be difficult to use this arrangement in order to specify the position of a portion to be inspected. On the other hand, when an ultrasonic wave 2102B is transmitted directly to a penetration 2104B adjacent to the penetration 2103B to be inspected, a reflected echo can be received. In this case, since the ultrasonic wave 2102B is directly transmitted to the reflection source, it is expected that the intensity of the echo received is sufficient. Thus, it is possible to use this arrangement in order to specify the position of a portion to be inspected.

Thirdly, in the case where the reactor pressure vessel and the penetration are arranged with a certain angle (e.g., 20 degrees or more) formed between them, the inner surfaces of the reactor pressure vessel and the penetration intersect each other with an obtuse angle (see FIG. 21C). In this case, it is difficult, in terms of geometry, to obtain a reflected wave from a region in which the inner surfaces of the reactor pressure vessel and the penetration intersect each other with the obtuse angle. Thus, a reflected echo can be received by transmitting an ultrasonic wave 2101C directly to the inner surface of the penetration 2103C from the ultrasonic probe 2105. Since the ultrasonic wave is also transmitted directly to the penetration 2103C, it is expected that the intensity of the reflected echo is sufficiently high when it is received. This makes it possible to specify the position of a portion to be inspected. When an ultrasonic wave 2102C is transmitted to a region in which the inner surface of the reactor pressure vessel intersects the inner surface of a penetration 2104C adjacent to the penetration 2103C to be inspected, a reflected echo may be received. The intensity of the reflected echo may be insufficient when it is received. Thus, it may be difficult to use this arrangement in order to specify the position of a portion to be inspected.

Using either or both of the two types of echoes (2101A to 2101C and 2102A to 2102C shown in FIGS. 21A to 21C), evaluation is performed to specify the position of a portion to be inspected in the next step S1105. Before the evaluation, however, it is necessary to confirm that the propagation direction of the ultrasonic wave transmitted from the ultrasonic probe 101 is present in a cross section 2201 shown in FIG. 22. That is, the ultrasonic probe 101 is rotated by the probe rotation mechanism 905 of the scanning mechanism 105 to adjust the rotational position of the ultrasonic probe 101 so that at least either one of the two types of the echoes shows a maximum intensity in step S1104B.

When least either one of the two types of the echoes (2101A to 2101C and 2102A to 2102C shown in FIGS. 21A to 21C) caused by the inner surface of the penetration shows the maximum intensity, the process proceeds to the next step S1104. Using the two types of echoes, the angle (inclination angle) formed between the reactor pressure vessel and the penetration is evaluated in step S1105. Based on the measured inclination angle, the position of a portion to be inspected (circumferential direction position of the penetration) is specified in step S1106. Details of steps S1105 and S1106 are described later.

After the transmission and reception of the ultrasonic waves in the plurality of directions, if an echo other than the echoes caused by the abovementioned shapes is not obtained, it is determined that a portion at the specified position of the portion to be inspected is in a good state. If another echo is obtained, it is determined that a defect is present in step S1107. In order to confirm the presence of a defect in detail, the position and dimension of the reflection source are evaluated based on the reception time of and the angle of a reflected wave in terms of an echo which is not caused by the shapes in step S1109. In general, it is determined whether or not the portion at the specified position is a good state through comprehensive determination made by several methods (e.g., using a frequency, angle, and position at which a sensor is arranged). Thus, in the flow chart shown in FIG. 11, after it is determined whether or not a defect is present and after the position and dimension of the reflection source is evaluated, the process is completed. Details of step S1109 will be described later.

Steps S1105 and S1106 shown in FIG. 11 will be described below with reference to FIGS. 2A and 12. FIG. 2A is a diagram illustrating an example of wave forms of and a cross sectional image of received echoes which are caused by the shapes of the reactor pressure vessel and the penetration. It should be noted that the echo 109 caused by the inner surface of the penetration shown in FIG. 2A is an example of the echoes directly transmitted to the inner surface of the penetration and corresponds to the ultrasonic wave 2102B shown in FIG. 21B or the ultrasonic wave 2102C shown in FIG. 21C.

The cross sectional image showing a portion to be inspected is drawn in accordance with a scanning axis direction (parallel to a surface to be inspected) and a depth direction (perpendicular to the surface to be inspected). Ultrasonic waves that are transmitted and received in a plurality of angular directions are drawn in directions in which signals thereof are transmitted and received. The ultrasonic waves drawn on the cross sectional image are displayed. Thus, as shown in FIG. 1, the positional relationship between the inner surface 113 of the reactor pressure vessel 103 and the echo 110 generated from the inner surface 113, and the positional relationship between the inner surface 112 of the penetration and the echo 109 generated from the inner surface 112, are provided without any change in position. It should be noted that even if an ultrasonic wave is transmitted and received in one direction, it propagates within an angle range called a directivity angle. The echoes from the inner surface 113 of the reactor pressure vessel 103 and from the inner surface 112 of the penetration are spread in the directions of the transmission and reception of the ultrasonic waves on the cross sectional image.

A description will be made of a method of determining the direction of the transmission and reception of each of the ultrasonic waves with reference to "received waves" shown in FIG. 2A. The direction of the transmission and reception is orthogonal to the inner surface of the penetration. Reference numerals 207A to 207C denote waves received in the transmission/reception directions 201A to 201C, respectively. A signal 203, which is first received, indicates an echo that means the surface of a portion to be inspected. An echo 204 present between time gates 205 and 206 is caused by the shape. In this case, a distance of the propagation can be calculated based on a propagation time 202 and on a velocity of an ultrasonic wave in a material of a portion to be inspected. With paying attention to the intensity of the echo 204 caused by the shape, as the transmission/reception direction is changed from 201A to 201C, the intensity of the echo 204 in the direction 201B, which is the middle position between the directions 201A and 201C, is maximum. The direction showing the maximum intensity is determined as the direction of the transmission and reception of the ultrasonic waves, the direction being orthogonal to the surface of the penetration. A direction 201 perpendicular to the direction 201B is evaluated as an angle of the inner diameter of the penetration.

Similarly, a direction 202 of transmission and reception of an ultrasonic wave, as shown in FIG. 2A, is varied while the direction 202 is the center between the rightmost and leftmost directions, which are obtained by changing the transmission/reception direction of the ultrasonic wave. A transmission/reception direction showing a maximum value of the echo intensity is determined as a direction opposite to the inner surface of the reactor pressure vessel. A direction 110 perpendicular to the direction showing the maximum value of the echo intensity is evaluated as a direction forming an inclination angle of the inner surface of the reactor pressure vessel. Since the surface scanned by the ultrasonic probe is typically parallel to the inner surface of the reactor pressure vessel, the direction 110 is horizontal. Thus, the inclination angle of the inner surface of the penetration is defined by using a surface to be inspected as a reference, not by using the direction 110.

It should be noted that an echo 110A obtained from the inner surface of the reactor pressure vessel and a propagation time 110B may be used to calibrate the ultrasonic probe 101 and the display unit 108 by use of information on the thickness of the reactor pressure vessel and on a positional relationship (in a horizontal direction) with the surface to be inspected.

Figure 12:
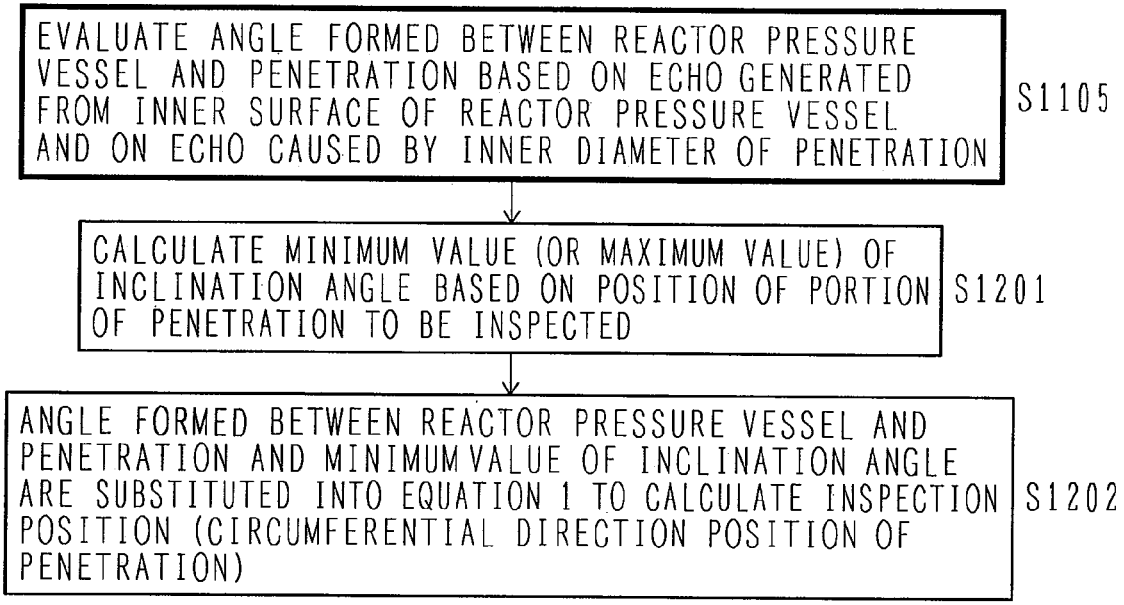
FIG. 12 is another flowchart according to the first embodiment of the present invention.

FIG. 12 is a flow chart for evaluating the position of a portion to be inspected in the case of using an ultrasonic wave (2102B shown in FIG. 21B or 2102C shown in FIG. 21C) directed to the inner surface of the penetration. As described above, the angle (inclination angle) formed between the reactor pressure vessel and the penetration is measured by use of an ultrasonic wave in step S1105. Next, the minimum value (or the maximum value) of the inclination angle is calculated from a position of the penetration, which has been specified in step S1101 and is to be inspected, in step S1201. Based on the angle, for example, a design drawing (two-dimensional cross section) or CAD data (two- or three-dimensional data) can be obtained. Lastly, the measured inclination angle ($\theta_{inclination}$)

and the calculated minimum value ($\theta_{MIN}$) are substituted into equation 1 to obtain the position of a portion to be inspected, i.e., the circumferential direction position of the penetration (when the position is expressed as an angle in the circumferential direction, it is $\theta_{circumferential\ direction}$ expressed by equation 1).

$$\theta_{circumferential\ direction} = \cos^{-1}(-\cos\theta_{inclination}/\sin\theta_{MIN}) \quad \text{Equation 1}$$

where, each of the words means as follows.

Figure 13:
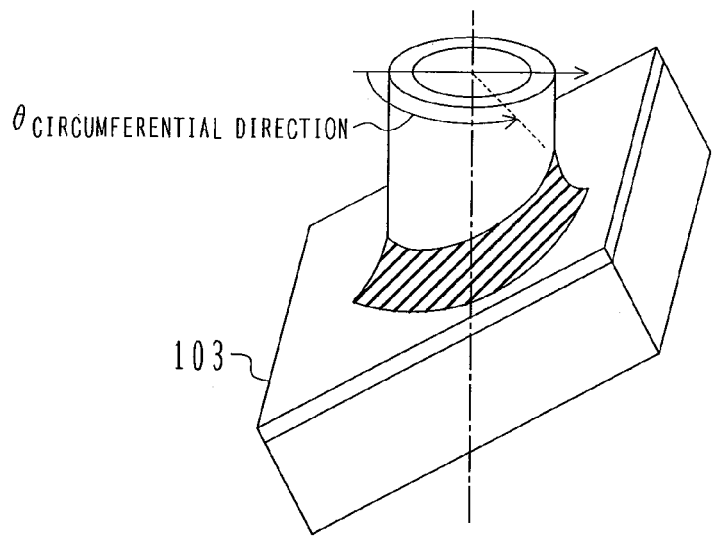
FIG. 13 is a diagram explaining variables used in equation 1.
Figure 14:
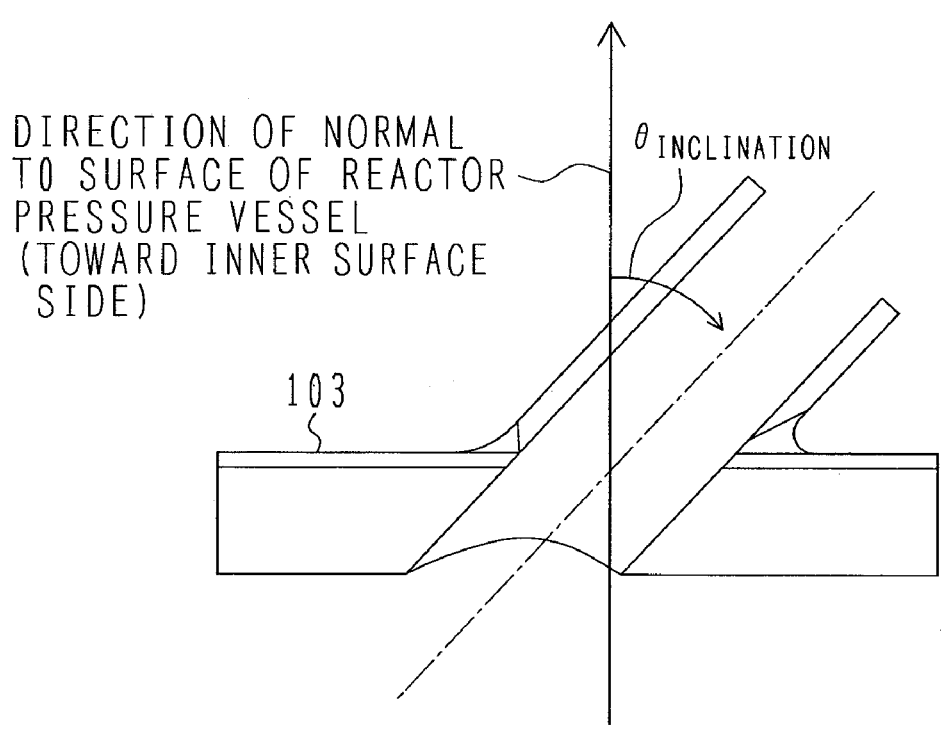
FIG. 14 is another diagram explaining variables used in equation 1.

$\theta_{circumferential\ direction}$: circumferential direction position (or angle) of the penetration;

$\theta_{inclination}$: angle formed between the reactor pressure vessel and the penetration (a measured value of the inclination angle); and $\theta_{MIN}$: minimum value of the angle formed between the reactor pressure vessel and the penetration FIG. 13 is a diagram showing the definition of the circumferential direction position (angle) $\theta_{circumferential\ direction}$ which is used in equation 1. In FIG. 13, the angle $\theta_{circumferential\ direction}$ is increased in a clockwise direction when viewed from the outer surface of the reactor pressure vessel as the circumferential direction is directed from the inner side toward the outer side (on the assumption that when the circumferential direction is directed to the inner side, the angle $\theta_{circumferential\ direction}$ is 0 degree). FIG. 14 is a diagram showing the definition of the angle $\theta_{inclination}$ (and $\theta_{MIN}$). The angle $\theta_{inclination}$ is formed between the direction of a normal line of the reactor pressure vessel and the axial direction of the penetration. The direction of the normal line of the reactor pressure vessel is defined as zero degree.

Figure 25:
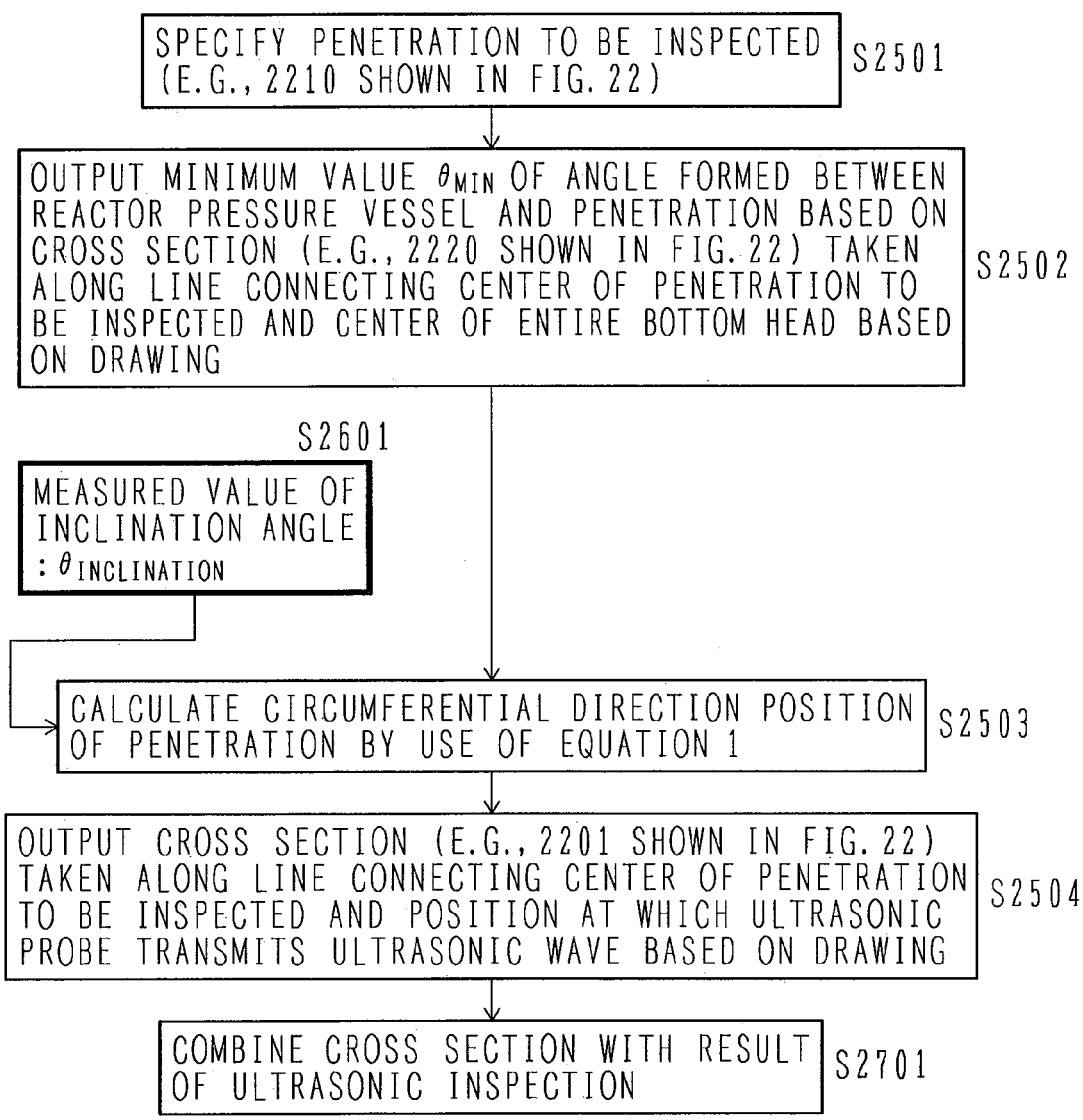
FIG. 25 is a flowchart according to the first embodiment of the present invention.

Although the process (steps 1201 and 1202) shown in FIG. 12 can be performed through manual calculation, it is assumed that when an actual inspection is performed, information provided in a drawing showing an apparatus to be inspected and dimensions of the apparatus are quantified before performing the inspection. In the case where the shapes of portions of the apparatus to be inspected, which are shown in a drawing, are quantified, the calculator 106F which is a computer can be used to automatically perform arithmetic processing in accordance with steps shown in FIGS. 25 to 27.

First, a penetration to be inspected is specified (e.g., a penetration 2210 shown in FIG. 22) in step S2501. Next, from a cross section obtained based on a line (e.g., a line 2220 shown in FIG. 22) connecting the center of the penetration to be inspected and the center of the entire bottom head, the minimum value $\theta_{MIN}$ of the angle formed between the pressure vessel and the penetration to be inspected is output based on the drawing in step S2502. Specifically, the angle may be manually or automatically calculated based on the drawing. Then, using the measured inclination angle obtained in step S2601, the circumferential direction position $\theta_{circumferential\ direction}$ of the penetration is calculated by use of equation 1. After the circumferential direction position of the penetration is determined, a cross sectional image obtained by connecting the center of the penetration to be inspected and the position at which the ultrasonic probe 101 transmits an ultrasonic wave is output based on a drawing showing an entire portion to be inspected and dimensions provided in the drawing in step S2504. Lastly, the cross sectional image and a result of the ultrasonic inspection are combined and displayed in step S2701, which will be described in detail later.

Next, a description will be made of measurement of the inclination angle with reference to FIG. 26. The measurement of the inclination angle is performed in step S2601. The measurement can be selected between manual measurement and automatic measurement performed by the calculator in step S2602.

Figure 26:
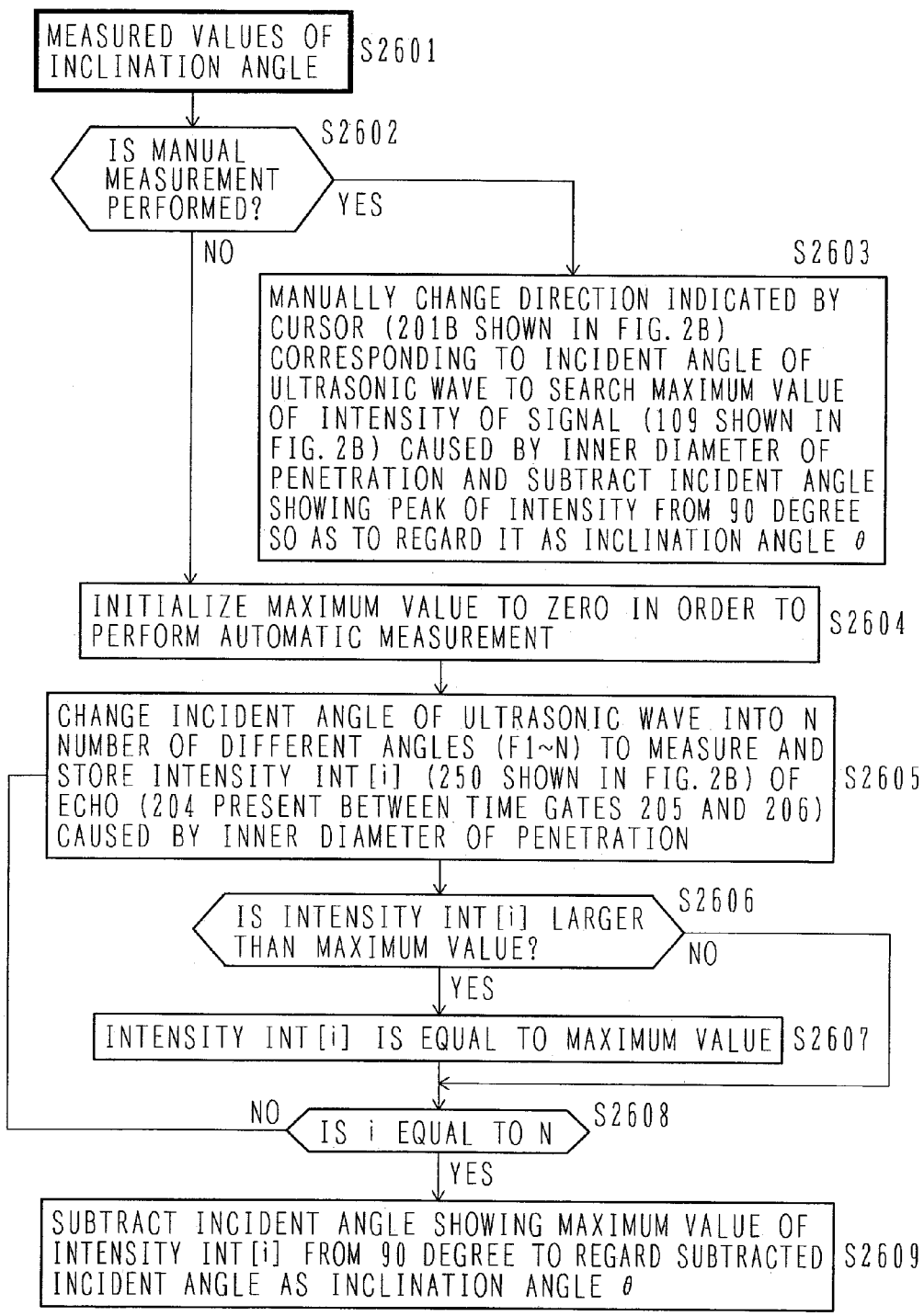
FIG. 26 is another flowchart according to the first embodiment of the present invention.

When the manual measurement is selected in S2602, the process shown in FIG. 26 proceeds to step S2603. In step S2603, an instruction item (angle cursor 201B shown in FIG. 2B) indicating an incident angle of the ultrasonic wave is manually changed while searching the maximum value of the intensity of a signal caused by the inner diameter of the penetration. Then, the incident angle of the ultrasonic wave, which shows a peak of the intensity, is subtracted from 90 degrees to obtain the incident angle θ.

When the automatic measurement is selected in S2602, the process shown in FIG. 26 proceeds to step S2604. In step S2604, the maximum value is first initialized to zero because processing in step S2604 is automatically performed. After the initialization, the incident angle of the ultrasonic wave is changed into N number of different angles (typically, N is about several ten to a hundred) in step S2605. While the incident angle is changed from a first angle to an Nth angle, the intensity of an echo caused by the inner diameter of the penetration, or the intensity of the echo 204 present between the time gates 205 and 206 is measured and stored in step S2605. From the intensities corresponding to the first to Nth angles, the maximum value of the intensity is searched in steps S2606 and S2607. The maximum value of the intensity is subtracted from 90 degrees to obtain the inclination angle θ in step S2609.

Figure 27:
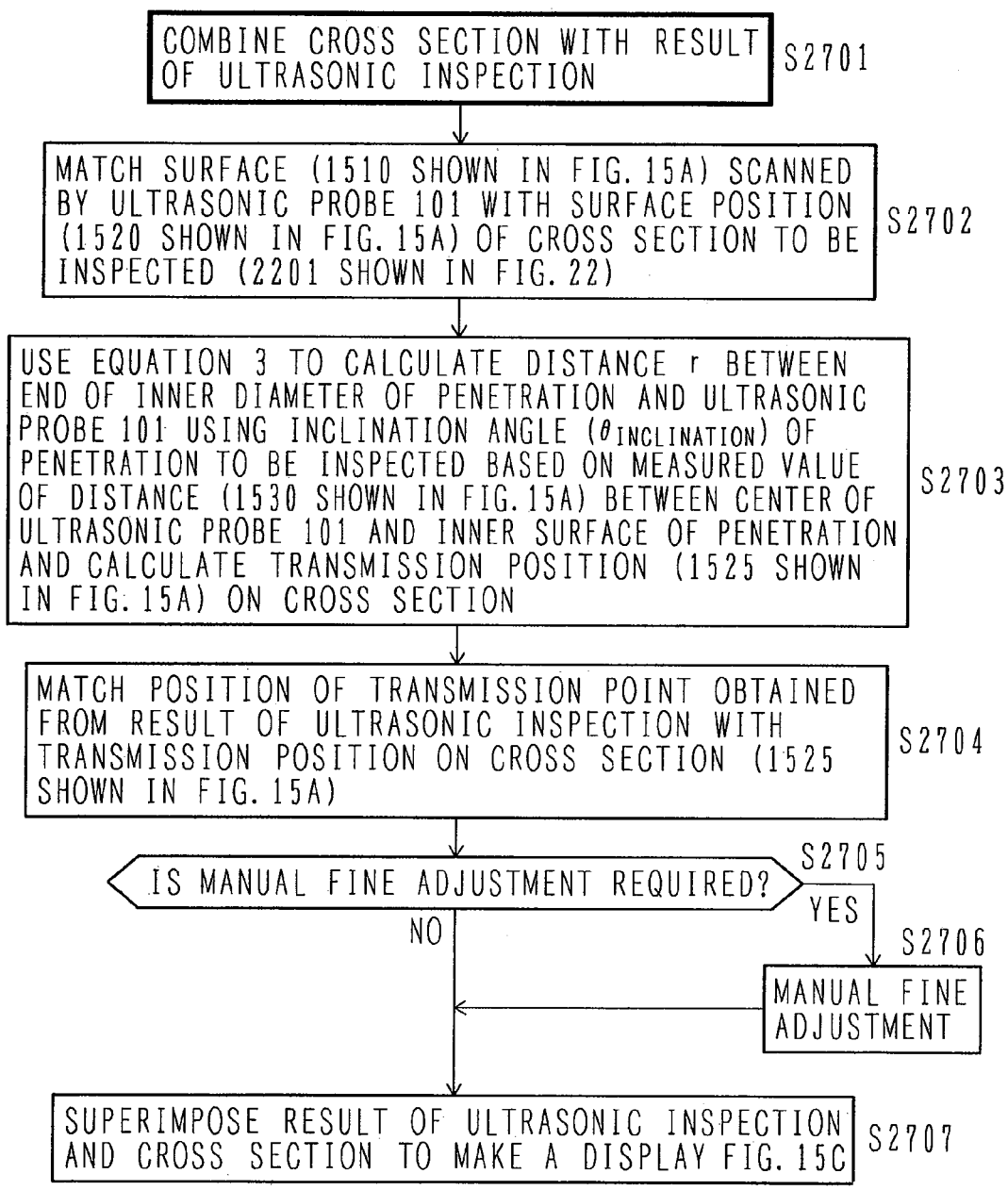
FIG. 27 is another flowchart according to the first embodiment of the present invention.

Next, a description will be made of step S2701 in which the inclination angle is measured, with reference to FIG. 27. The purpose of the process shown in FIG. 27 is to cause the surface scanned by the ultrasonic probe 101 upon the ultrasonic inspection to coincide with the cross sectional image (obtained based on the line 2201 shown in FIG. 22) which is to be inspected so as to make a display.

First, when performing the inspection, the surface (1510 shown in FIG. 15A) scanned by the ultrasonic probe 101 is caused to coincide with the position of the surface shown in the cross sectional image (1520 shown in FIG. 15A) and to be inspected in step S2702. For the inclination angle (θ) of the inner diameter of the penetration to be inspected, a distance between the center of the ultrasonic probe 101 and the end of the inner diameter of the penetration to be inspected is measured. Based on the measured distance, a distance between the end of the inner diameter of the penetration and the ultrasonic probe 101 is calculated by using equation 3 to obtain a position (1525 shown in FIG. 15A) at which the ultrasonic probe 101 transmits an ultrasonic wave on the cross sectional image in step S2703. Each symbol and each word used in equations 2 and 3 are described in FIG. 31. The position (1515 shown in FIG. 15A) of the transmission performed by the ultrasonic probe 101 based on the result of the inspection is placed to coincide with the calculated position (1525 shown in FIG. 15A) of the transmission on the cross sectional image.

$$L(r) = r\sqrt{1 - \cos^2\theta_{circumferentialdirection}\cos^2\theta_{MIN}} - D/2 \quad \text{Equation 2}$$

$$r = \frac{L_{measuredvalue}}{\sqrt{1 - \cos^2\theta_{circumferentialdirection}\cos^2\theta_{MIN}} - D/2} \quad \text{Equation 3}$$

With the above processes, alignment of both images in vertical and horizontal directions is completed. This uniquely defines the superposition of the images. Whether or not manual fine adjustment is necessary is confirmed by using a composite image in step S2704. The fine adjustment is performed if necessary in step S2705. After that, the result of the ultrasonic inspection is superimposed with the cross sectional image to display the composite image (e.g., an image shown in FIG. 15C).

The abovementioned description assumes that the relationship of the penetrations 2103A to 2103C with the penetrations 2104A to 2104C respectively adjacent to the penetrations 2103A to 2103C is applied to the case shown in FIG. 21C, or the case where a penetration to be inspected coincides with a penetration with a reflection surface on which an ultrasonic wave used to measure an inclination angle of the penetration is reflected.

A description will be made of the case where a penetration to be inspected does not always coincide with a penetration whose inclination angle is to be measured and where an echo directly transmitted from an inner surface of a penetration adjacent to the penetration to be inspected is used. In this case, when viewed from the ultrasonic probe, the penetration to be inspected and the reactor pressure vessel intersect at an obtuse angle. Also, in this case, it is difficult to receive an echo that is directly transmitted from the inner surface of the penetration.

Figure 15B:
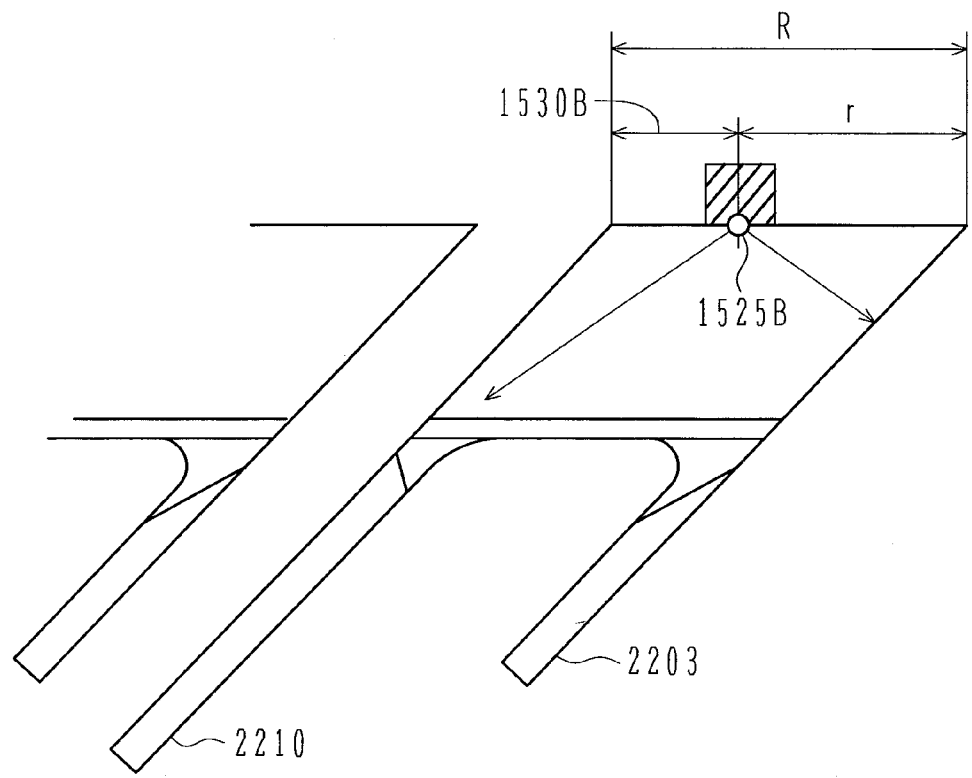
FIG. 15B is an explanatory diagram showing an example of a result of the ultrasonic inspection according to the embodiments of the present invention.

FIG. 15B is a diagram showing an example of the positional relationship of a penetration adjacent to a penetration to be inspected with the penetration to be inspected. Similarly to the case shown in FIG. 15A, based on a measured distance between a penetration 2210 to be inspected and the end of the inner diameter of the penetration 2203 adjacent to the penetration 2210, a distance (r shown in FIG. 15B) between the end of the inner diameter of the penetration and the ultrasonic probe 101 is calculated by using equation 3. After that, as instructed in a drawing or the like showing a portion to be inspected, the calculated distance r is subtracted from a distance (R shown in FIG. 15B) between the end of the inner diameter of the penetration 2210 to be inspected and the end of the inner diameter of the penetration 2203 adjacent to the penetration 2210. Then, a distance 1530B between the end of the inner diameter of the penetration 2210 to be inspected and the ultrasonic probe 101 is calculated. The calculated distance 1530B is regarded as the position at which the ultrasonic probe 101 transmits an ultrasonic wave. Using the position of the transmission, the inspection image and the cross section are superimposed based on the flowchart shown in FIG. 27.

Figure 15C:
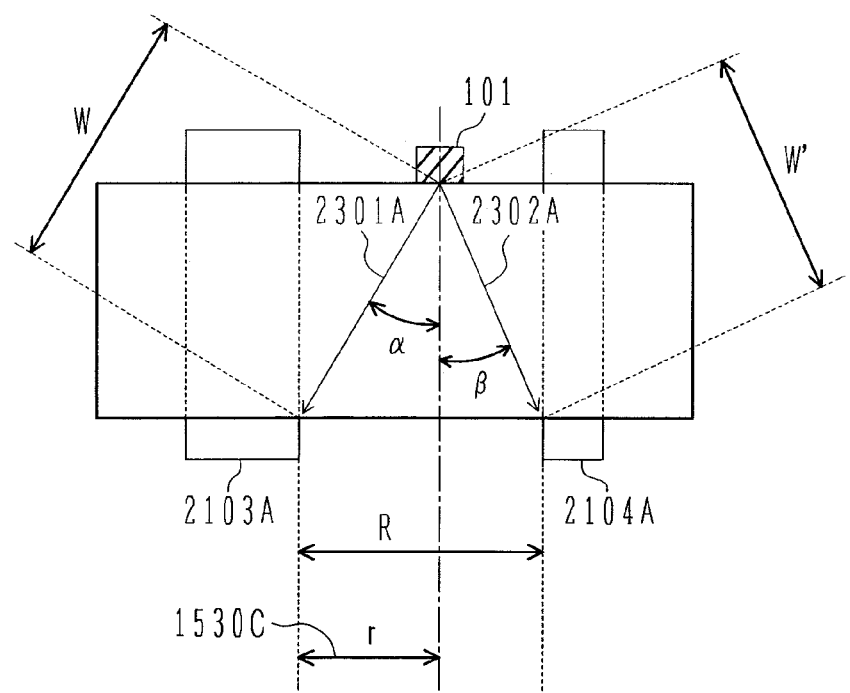
FIG. 15C is an explanatory diagram showing an example of a result of the ultrasonic inspection according to the embodiments of the present invention.

FIG. 15C is a diagram showing an example of the case where a penetration to be inspected does not always coincide with a penetration adjacent to the penetration to be inspected and where an echo transmitted from a region in which the penetration to be inspected and the penetration adjacent to the penetration intersect the reactor pressure vessel is used. In this case, the penetrations and the reactor pressure vessel intersect substantially at a right angle.

Assume the case where ultrasonic waves (2101A and 2102A shown in FIG. 21A) transmitted to regions in which the inner surface of the reactor pressure vessel intersects inner surfaces of the penetrations are used. As shown in FIG. 15C, a propagation distance of an echo (W or W') transmitted from a region in which the reactor pressure vessel intersects a penetration 2303A to be inspected or a penetration 2304A adjacent to the penetration 2303A is measured. Using equation 4 or 5 described below, a distance between the end of the inner diameter of the penetration and the position at which the ultrasonic probe 101 transmits an ultrasonic wave is measured. Then, the result of the inspection and the cross section are combined.

$$r = W \sin \alpha \qquad \text{Equation 4}$$

$$r = R - W' \sin \beta \qquad \text{Equation 5}$$

In the case of using equation 4, the calculated distance r may be used without performing another calculation. In the case of using a penetration adjacent to a penetration to be inspected, or in the case of using equation 5, the result of the calculation based on equation 5 is subtracted from the distance (R shown in FIG. 15C) between the end of the inner diameters of the penetrations to obtain a desired value, or the distance between the end of the inner diameter of the penetration to be inspected and the position at which the ultrasonic probe transmits an ultrasonic wave in a similar manner to the above-mentioned case described with reference to FIG. 15B.

As described above, in the case where a penetration to be inspected is specified, the position of a portion (to be inspected) of the penetration in the circumferential direction of the penetration can be identified in accordance with the inclination angle of the penetration relative to the reactor pressure vessel, the inclination angle having been measured by using an ultrasonic wave. Conventionally, due to a thick plate of a reactor pressure vessel, it has been difficult to determine the position of a portion of a weld in a reactor pressure vessel, the portion being under inspection. According to the present invention, however, the position of a portion (to be inspected) of a weld in a reactor pressure vessel can be identified.

Figure 19:
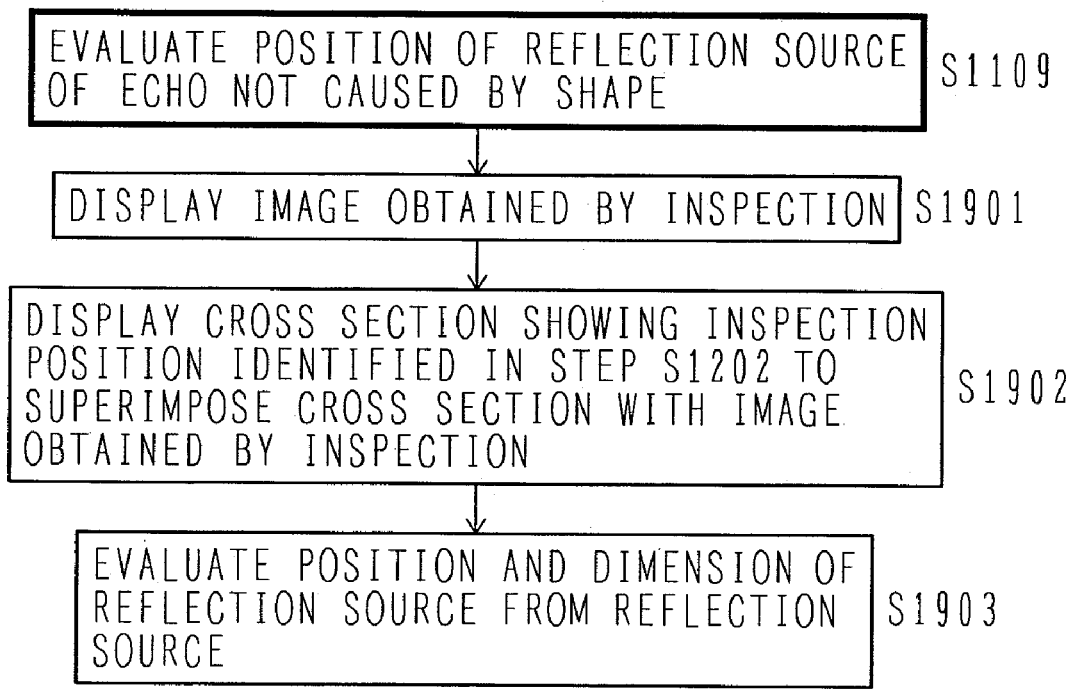
FIG. 19 is a flowchart according to the first embodiment of the present invention.

In the last part of the description of the present embodiment, step S1109 shown in FIG. 11 will be described with reference to FIGS. 15A and 19. FIG. 15A is a flowchart relating to an example of an inspection image in the case of performing an ultrasonic inspection using an ultrasonic wave transmitted from the outer surface of the reactor pressure vessel. The flowchart shown in FIG. 19 represents details of step S1109. As shown in FIG. 19, the flowchart includes three steps: step 1901 of displaying an image obtained by performing an ultrasonic inspection; step 1902 of superimposing the image with the cross section; and step 1903 of measuring the position and dimension of a reflection source. Hereinafter, the steps shown in the flowchart will be described using an example of an image showing the ultrasonic inspection.

FIG. 15A is a schematic diagram showing an image obtained by performing the ultrasonic inspection. As described above, the echo 109 is generated from the inside of the penetration. When an ultrasonic wave is transmitted and received in a direction 201B, the highest intensity of the echo 109 can be obtained. A direction orthogonal to the direction 201B is used to calculate the inclination angle of the penetration relative to the reactor pressure vessel. An example of an image obtained by performing the ultrasonic inspection is shown in FIG. 15A (B). Among echoes (1501 to 1503) observed in FIG. 15A (B), the echo 1501 corresponds to the echo 109. When an ultrasonic wave is transmitted and received in a direction 1507, the highest intensity of the echo 109 can be obtained. A direction orthogonal to the direction 1507 can be used to calculate the inclination angle of the penetration relative to the reactor pressure vessel. Based on the inclination angle and a drawing used when a design is performed, a cross sectional image 1504 showing a portion to be inspected is created. Then, the created image is superimposed with the image obtained by performing the ultrasonic inspection to make a display.

As described above, the result of the ultrasonic inspection, which includes an echo caused by at least the shape of the penetration, is combined and compared with a drawing (cross sectional image) showing a portion to be inspected. According to the comparison, the echo 1503 substantially coincides with the contour line of the surface of a weld when viewed from the inner surface of the reactor pressure vessel. Thus, it is understood that the echo 1503 is present near the surface (curved surface portion) of the weld. On the other hand, since it can be seen that the echo 1502 is present at a central portion of the weld, there is a high possibility that the reflection source may be defective or present at an edge portion of the weld. With the superimposition of the image obtained by performing the ultrasonic inspection with the design drawing, a depth 1506 from the surface of the weld for the reflection source (corresponding to the echo 1503) and a depth 1505 from the outer surface (inspection surface) of the reactor pressure vessel can be measured. If the reflection source is defective, the depths can be used to evaluate the safety in consideration of a progress of the defect. In the present embodiment, the description has been made by use of the diagram shown in FIG. 15A. A similar comparison and review can be performed in the cases of FIGS. 15B and 15C.

In the first embodiment of the present invention, the method and apparatus for measuring the position and dimension of the reflection source are provided. According to the first embodiment, the ultrasonic probe is placed on the outer surface of the reactor pressure vessel to measure the angle (inclination angle) formed between the reactor pressure vessel and the penetration so that the position of a portion to be inspected by using an ultrasonic wave is identified. Then, an inspection image indicating the position of a portion to be inspected is compared with the design drawing to measure the position and dimension of the reflection source.

Second Embodiment

Figure 3:
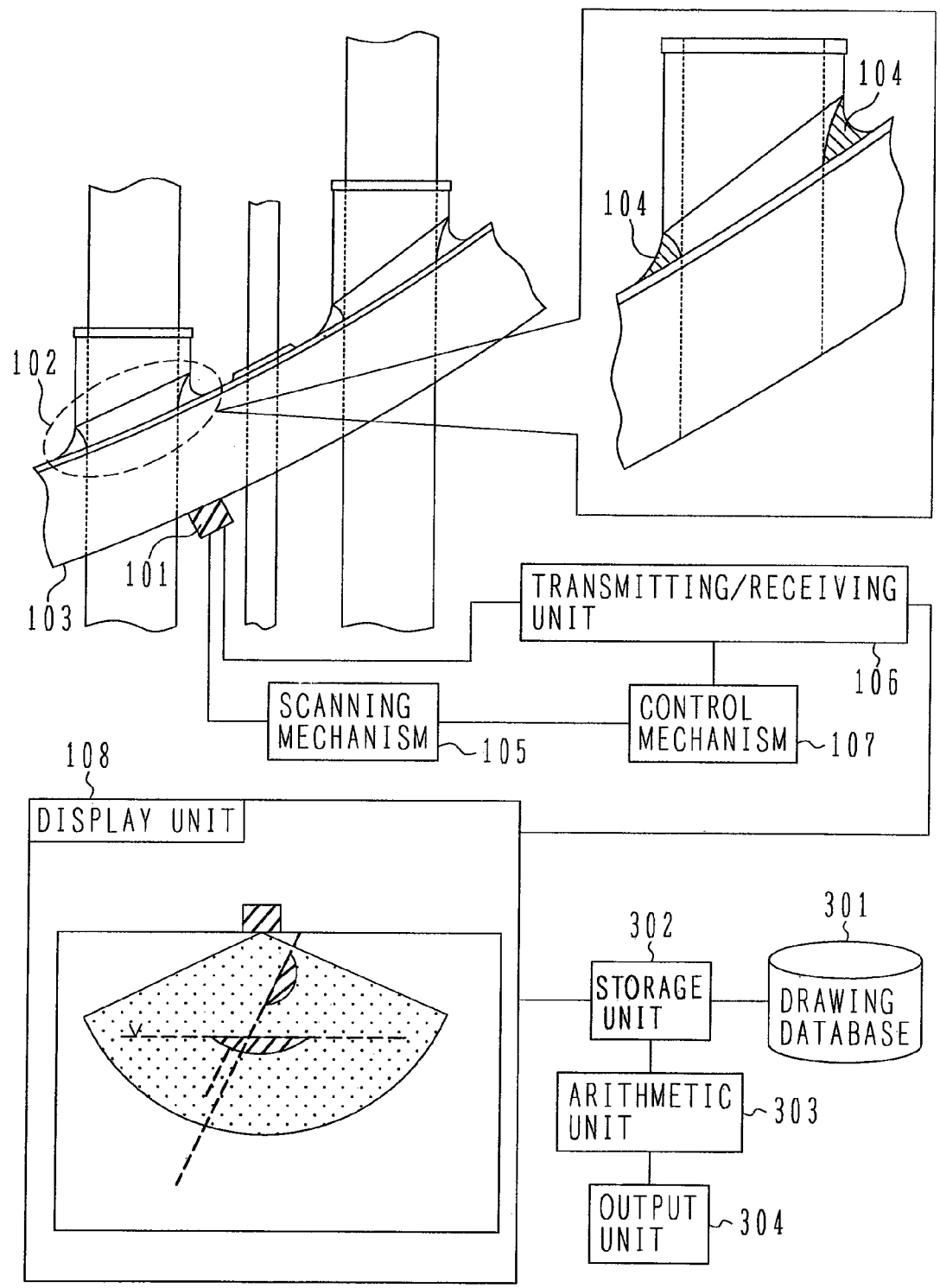
FIG. 3 is a diagram showing the configuration of an ultrasonic inspection apparatus according to a second embodiment of the present invention.

FIG. 3 is a diagram showing a second embodiment of the present invention. As shown in FIG. 3, the second embodiment is the same as the first embodiment in that the ultrasonic probe 101 that receives an ultrasonic wave through the reactor pressure vessel 103 is pushed to the outer surface of the reactor pressure vessel 103 so as to inspect a target portion 102 (shown in a circle indicated by a broken line).

The second embodiment differs from the first embodiment in that an ultrasonic inspection apparatus has a drawing database 301, a storage unit 302, an arithmetic unit 303, and an output unit 304. The storage unit 302 stores the relationship (master curve as shown in FIG. 8) of the circumferential direction of the penetration with an angle (inclination angle) formed between the reactor pressure vessel and the penetration. In order to create the master curve, information stored in the drawing database 301 may be used.

The arithmetic unit 303 of a computer, which is adopted as a calculator, compares and calculates the inclination angle that has been measured by using an ultrasonic wave and the master curve so as to identify the position of a portion to be inspected by using an ultrasonic wave. The identified position that is to be inspected may be displayed by the output unit 304 as an angle or as a drawing by use of drawing information stored in the drawing database 301. The calculator 106F of the transmitting/receiving unit 106 according to the first embodiment may have such a function for performing a comparative calculation.

It should be noted that since the master curve stored in the storage unit 302 is theoretically defined by the one to one relationship of the circumferential direction of the penetration and the angle (inclination angle) formed between the reactor pressure vessel and the penetration, the position of a portion to be inspected can be obtained by drawing a normal line with respect to the X axis from the intersection of a measured value (Y axis) with the master curve to the X axis.

The second embodiment is the same as the first embodiment except that the master curve is used to identify the position of a portion to be inspected.

Third Embodiment

Figure 16:
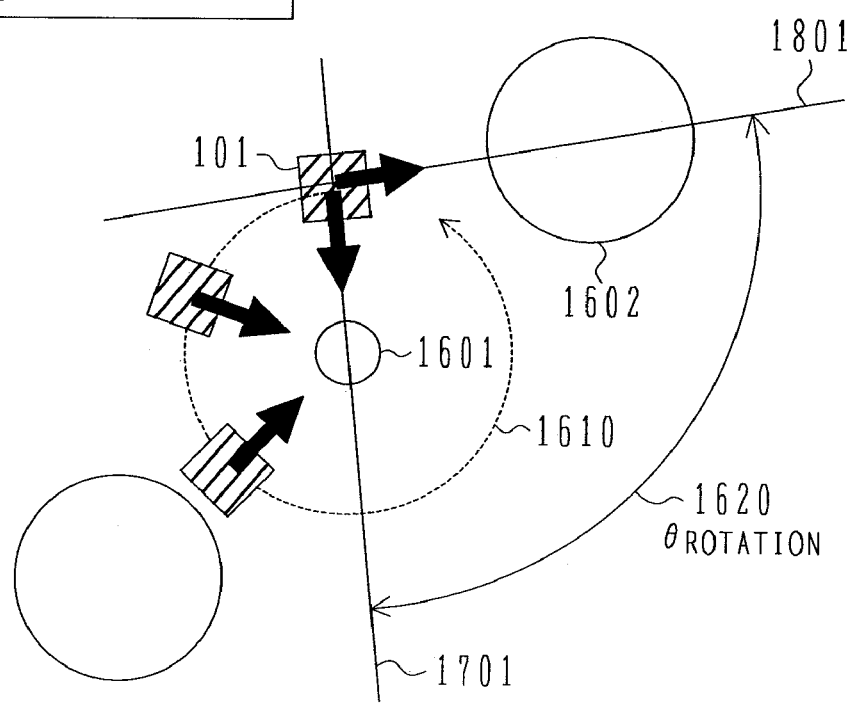
FIG. 16 is a diagram showing a third embodiment of the present invention.

A third embodiment of the present invention will be described with reference to FIG. 16. The third embodiment differs from the first and second embodiments in that, as shown in FIG. 24, a cross section formed by a line passing the centers of the ultrasonic probe 101 and a penetration 2410 to be inspected does not pass the centers of penetrations (2402 and 2403) in the vicinity of the penetration 2410. In general, such a case occurs, for example, when as shown in FIG. 16 the ultrasonic probe 101 scans an area to be inspected along a circle 1610 surrounding a penetration 1601 to inspect a welded portion.

It is necessary to clarify which portion of the penetration 1601 is inspected by the ultrasonic probe 101 to thereby identify the portion thereof. Specifically, in order to identify the position of the portion to be inspected, it is necessary to clarify the circumferential direction of the penetration 1601 to be inspected and the distance between the penetration 1601 and the ultrasonic probe 101.

Especially, in the case where a penetration (2410 in the case of FIG. 24, 1601 in the case of FIG. 24) which is to be inspected has been specified among all portions to be inspected (FIG. 24) since a drawing showing an apparatus that is to be inspected or the like is present, in order to identify the position of the ultrasonic probe 101 relative to the penetration 1601 that is to be inspected, the position of the ultrasonic probe 101 relative to a penetration (1602 in the case of the present embodiment) other than the penetration 1601 should be identified so that the position of the ultrasonic probe 101 is identified. In the first embodiment, the description has been made of the case where the penetration to be inspected, another penetration adjacent to the penetration to be inspected, and the ultrasonic probe 101 are placed on a single straight line (see FIGS. 21A to 21C and FIG. 22) as a special case among the cases of using a penetration other than the penetration to be inspected.

According to the third embodiment, when the position of a portion (to be inspected) of the penetration 1601 is evaluated, an ultrasonic wave transmitted and received by the ultrasonic probe 101 is varied in direction in order to use an inclination angle formed between the reactor pressure vessel and the penetration 1602 adjacent to the penetration 1601 to be inspected.

A device, method, procedure for obtaining the angle (inclination angle) formed between the reactor pressure vessel and the adjacent penetration 1602 are the same as those in the first and second embodiments.

Although as shown in FIG. 16 the penetration 1601 has a diameter smaller than that of the penetration 1602, the penetration 1601 and another penetration adjacent to the penetration 1601, or the penetration 1602 that is to be used to measure the inclination angle, may be the same in diameter in a description below. This is true for following descriptions.

FIG. 30 is a flowchart showing a process for evaluating the position of a portion to be inspected according to the third embodiment of the present invention. It should be noted that since the first three steps prior to step S3001 are the same as steps S1101 to S1103 of the process shown in FIG. 11, they are not shown in FIG. 30.

When a plurality of penetrations that are to be inspected using an ultrasonic wave are present, a penetration to be inspected is set in step S1101. After that, in order to inspect the penetration (1601) to be inspected, the scanning mechanism 105 is moved to an area near the penetration to be inspected in step S1102. Next, the pushing mechanism 901 is used to push the ultrasonic probe 101 to the outer surface of the reactor pressure vessel 103 in step S1103.

The ultrasonic probe 101, which has been pushed to the outer surface of the reactor pressure vessel, transmits ultrasonic waves in a plurality of directions in step S3001. When a reflection source is present, an echo (reflected wave) is received from an angular direction of the reflection source.

Figure 18:
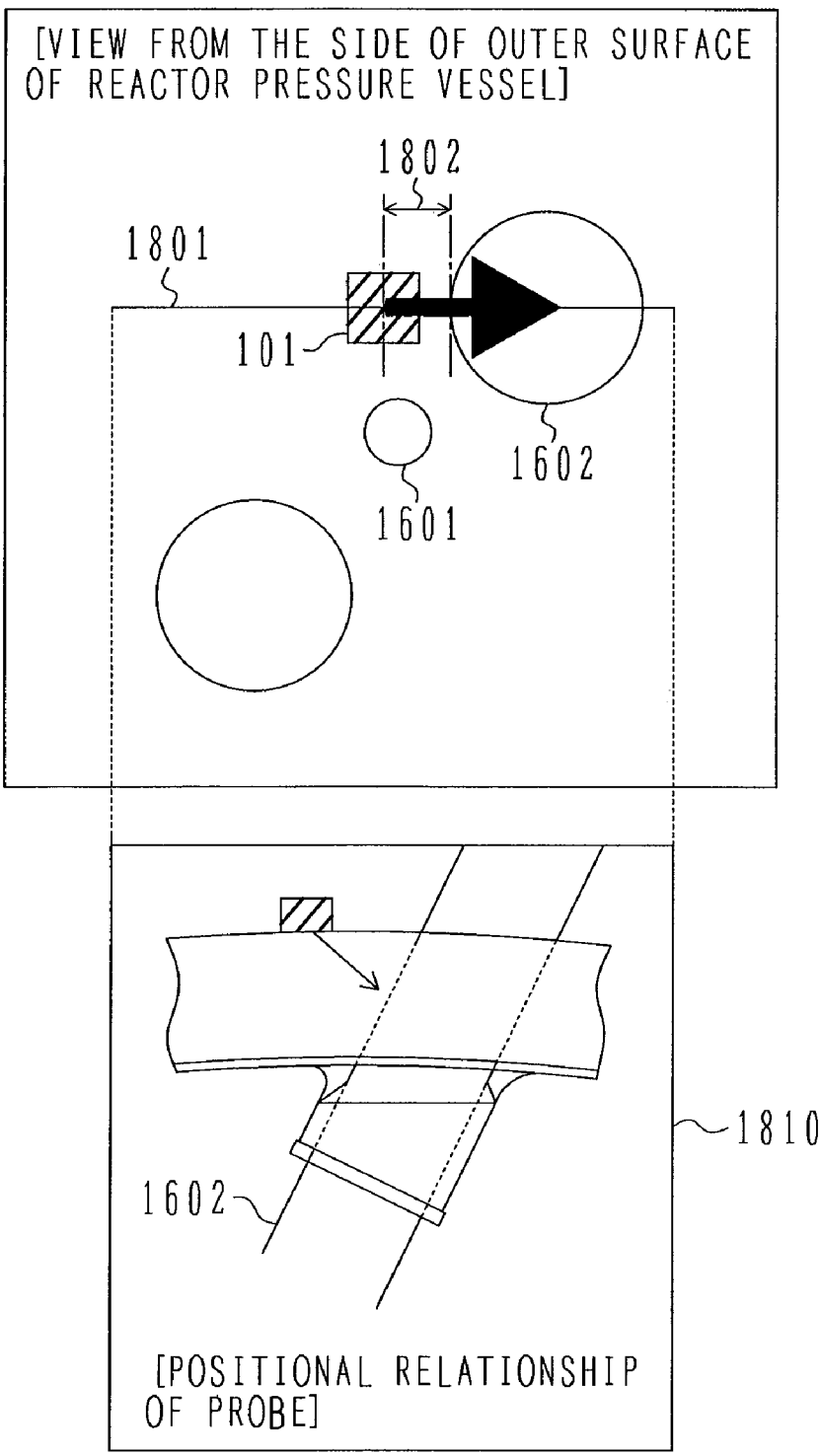
FIG. 18 is another diagram showing the third embodiment of the present invention.

In the present embodiment, as shown in FIGS. 16 to 18, the penetration to be inspected, the penetration used to identify the inspection position (i.e., the position and direction of the ultrasonic probe 101), and the ultrasonic probe 101 are not placed on a single straight line. Thus, it is necessary to identify the inspection position before performing the ultrasonic inspection on a target portion.

Figure 28:
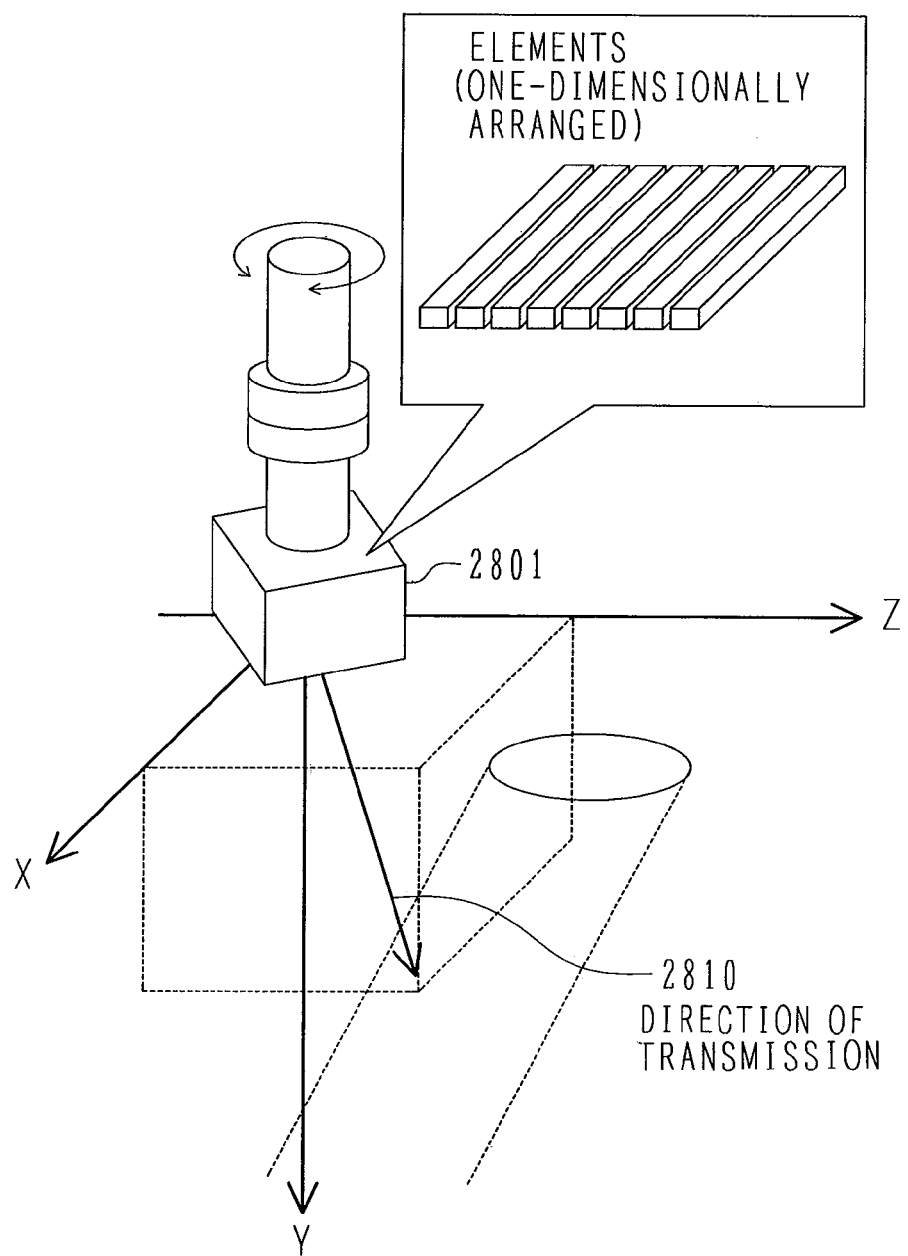
FIG. 28 is a diagram showing the third embodiment of the present invention.
Figure 29:
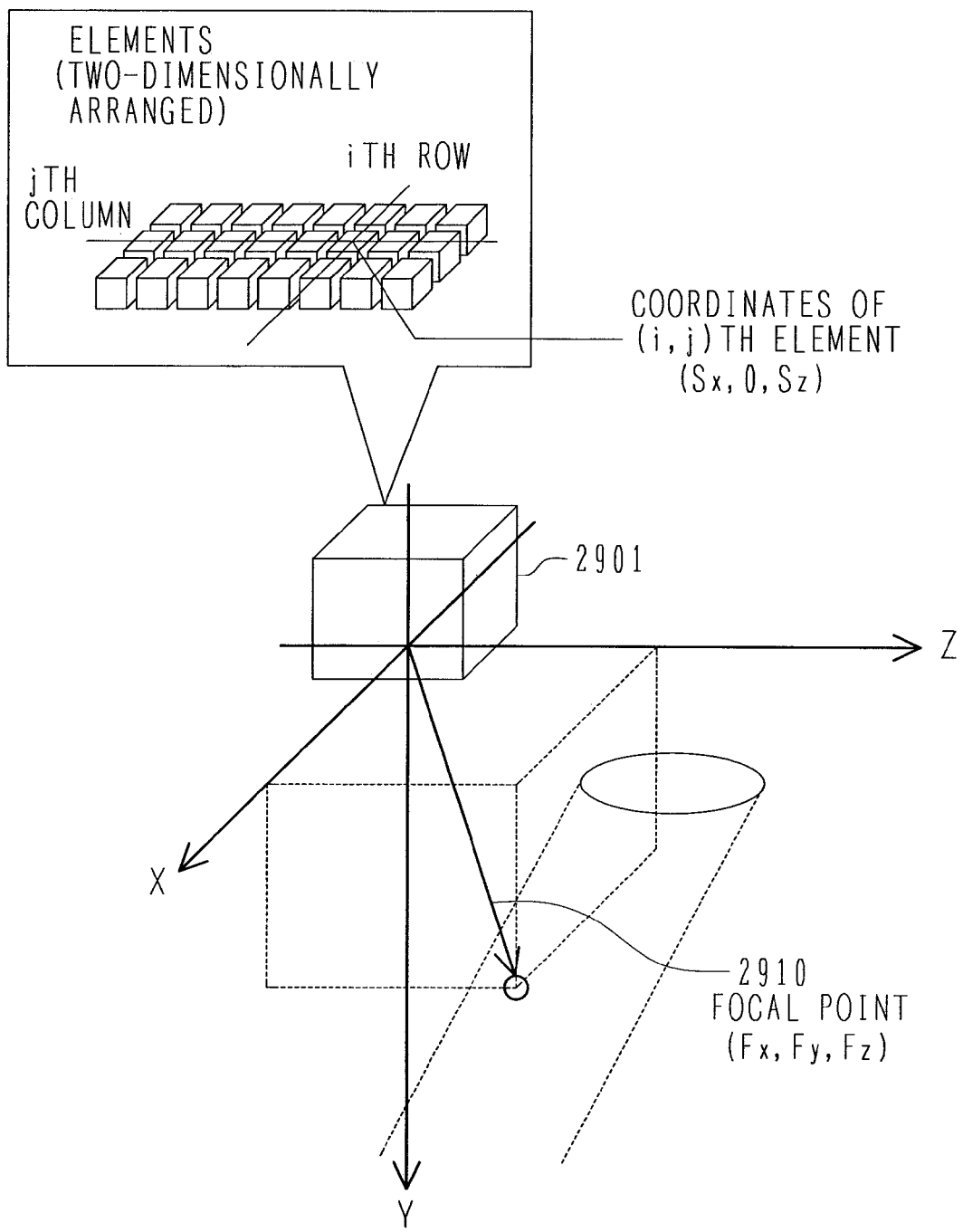
FIG. 29 is another diagram showing the third embodiment of the present invention.

In order to identify the inspection position, as shown in FIGS. 117 and 18 it is necessary to change the direction of transmission of an ultrasonic wave transmitted by the ultrasonic probe 101 so as to direct it to the penetration 1602 used to identify the inspection position (S3002). To change the direction of transmission of the ultrasonic wave, a mechanical technique (using a mechanical probe rotation mechanism indicated with reference numeral 905 as shown in FIG. 9) shown in FIG. 28 may be used. Alternatively, a matrix type array probe with elements two-dimensionally arranged in an array pattern may be used to electrically change the direction of the transmission.

In the case of the mechanical technique, the probe rotation mechanism 905 is used to physically rotate a probe 2801 so as to obtain a desired transmission direction 2810. In the case of the electrical technique, based on coordinates of each of elements forming a matrix type array probe 2901 and on coordinates of a focal point 2910 that is used as a reference of the transmission direction, the time for an ultrasonic wave to propagate between each of the elements and the focal point 2910 is calculated. A delay is supplied to each of the elements so that the ultrasonic wave that has been emitted from each of the elements forming the matrix type array probe 2901 reaches the focal point 2910, which makes it possible to control the transmission direction. Typically, the function for electrically controlling the transmission direction can be achieved by using the transmitting/receiving unit illustrated in the example of the system configuration shown in FIG. 20.

FIG. 17 is a diagram showing the ultrasonic probe 101 and the penetrations when viewed from the side of the outer surface of the reactor pressure vessel. In FIG. 17, reference numeral 1710 denotes a cross sectional view taken along line 1701 of FIG. 17. The line 1701 passes the penetration 1601 and the position at which the ultrasonic probe 101 transmits an ultrasonic wave. When viewed from the ultrasonic probe 101, the angle formed between the reactor pressure vessel and the penetration is obtuse. Thus, it is difficult to directly receive an echo from the inner surface of the penetration in the case of FIG. 17. The direction of transmission of an ultrasonic wave, however, is rotated by an angle θ (1620) as shown in FIG. 16. As shown in FIG. 18, a cross section view (1810) taken along line 1801 of FIG. 16 can be obtained. The line 1801 passes the center of a penetration 1602 adjacent to the penetration 1601 and the position at which the ultrasonic probe 101 transmits an ultrasonic wave. The case shown in the cross sectional view (1810) is similar to that shown in FIG. 15A. Therefore, the inspection position can be identified by the method similar to that in the first embodiment.

In the first embodiment, a penetration to be inspected and a penetration used to identify the inspection position are present on the same cross section. In the present embodiment, the above penetrations and the ultrasonic probe cannot be present on the same cross section simultaneously. The echoes (2101A to 2101C and 2102A to 2102C shown in FIGS. 21A to 21C) used to identify the inspection position correspond to echoes 2301A, 2302B, 2301C respectively shown in FIGS. 23A to 23C.

Any of signals corresponding to the above echoes is used to identify the inspection position in step S3005. Before performing step S3005, however, it is necessary to confirm whether the direction of propagation of the ultrasonic wave transmitted by the ultrasonic probe 101 is present on the cross section 1801 shown in FIG. 16, or on a cross section taken along a line passing an incident point of the ultrasonic wave transmitted by the ultrasonic probe 101 and the center of the penetration 2403 adjacent to the penetration to be inspected.

Using the probe rotation mechanism 905 of the scanning mechanism 105 or the array probe 2901 having the elements two-dimensionally arranged as the ultrasonic probe 101, the transmission direction of the ultrasonic wave transmitted by the ultrasonic probe 101 is rotationally adjusted while confirming whether the echo signal can be received in step S3003 and confirming whether the maximum intensity of the echo can be obtained in step S3004 when the echo signal can be obtained.

Figure 23A:
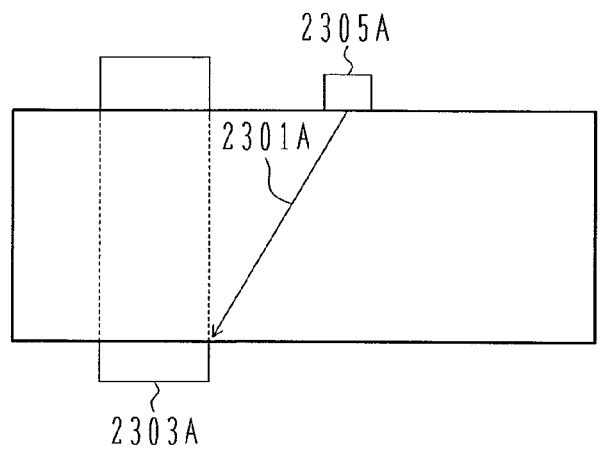
FIG. 23A is a diagram explaining the third embodiment of the present invention.
Figure 23B:
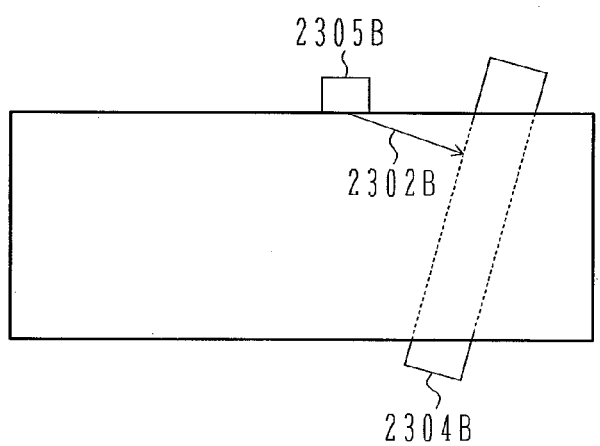
FIG. 23B is another diagram explaining the third embodiment of the present invention.
Figure 23C:
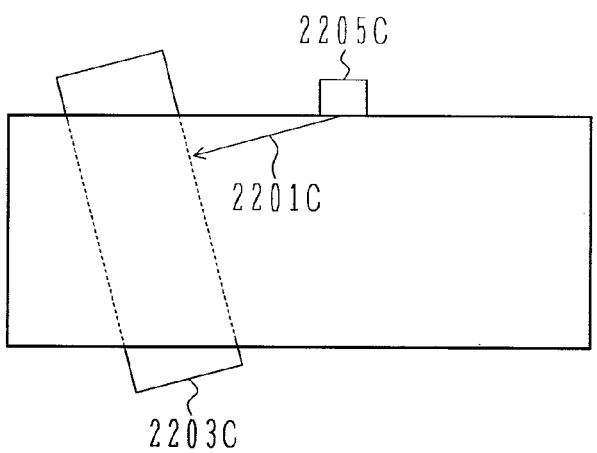
FIG. 23C is another diagram explaining the third embodiment of the present invention.

When any one of the echoes 2301A, 2301B, 2301C respectively shown in FIGS. 23A to 23C shows the maximum intensity, the process proceeds to the next step S3005. Using the echoes 2301A, 2301B, 2301C, the angle (inclination angle) formed between the reactor pressure vessel and the penetration is evaluated in step S1105. Based on the measured inclination angle, the position of a portion to be inspected (circumferential direction position of the penetration to be inspected) is identified in step S3006. It should be noted that details of steps S3005 and S3006 are the same as those in the first embodiment.

After identifying the position of the ultrasonic probe 101, the abovementioned mechanical technique or electrical technique is used to change the direction of the transmission of the ultrasonic wave so that the ultrasonic wave is transmitted toward the penetration to be inspected. Then, a target welded portion is inspected. In this case, steps S1107 to S1109 of determining whether the target welded portion is in a good state are the same as those in the first embodiment.

In the present embodiment, since the position (circumferential direction position) of the penetration to be inspected relative to the penetration 1602 is identified by the method described in the first embodiment, it can be identified that the ultrasonic probe 101 is present on the line of the cross section 1701 (or 1801). In addition, based on a distance 1508 (shown in FIG. 15A) between the end of the inner diameter of the penetration and the echo 109, a distance between the penetration 1602 adjacent to the penetration to be inspected and the ultrasonic probe 101 can be obtained.

Accordingly, the position of the ultrasonic probe can be identified by the method of identifying the position of the ultrasonic probe relative to the penetration described in the first embodiment and by using a penetration adjacent to the penetration that is to be inspected as a reference. According to the third embodiment of the present invention, the ultrasonic probe is placed on the outer surface of the reactor pressure vessel to measure the angle (inclination angle) formed between the reactor pressure vessel and the penetration. Based on the measured angle, even when the penetration to be inspected, the penetration adjacent to the penetration to be inspected, and the ultrasonic probe are not present on a single straight line, the inspection position can be identified with the adjacent penetration used as a reference by changing the direction of transmission of the ultrasonic wave. Therefore, the method and apparatus for measuring the position and dimension of a reflection source can be provided by comparing the inspection position with the design drawing.

What is claimed is:

1. A method of an ultrasonic inspection in which an ultrasonic probe of an ultrasonic inspection apparatus transmits an ultrasonic wave to a reactor pressure vessel and receives the ultrasonic wave that is reflected on a penetration of the reactor pressure vessel, and an echo based on the reflected ultrasonic wave is displayed on a display unit of the ultrasonic inspection apparatus, the method comprising:

a first step of calculating an inclination angle of the penetration relative to a wall surface of the reactor pressure vessel based on a result of the reception of the reflected ultrasonic wave; and a second step of calculating a circumferential direction position of the penetration having the inclination angle.

2. The method of an ultrasonic inspection according to claim 1, wherein the first step includes a step of subtracting an incident angle of the ultrasonic wave which provides the maximum intensity of the echo from 90 to obtain the inclination angle.

3. The method of an ultrasonic inspection according to claim 1, wherein the second step includes a step of solving an equation of the form, $\theta_{circumferential\ direction} = \cos^{-1}(-\cos\theta_{inclination}/\sin\theta_{MIN})$, to identify the circumferential direction position corresponding to the inclination angle, where $\theta_{circumferential\ direction}$ is the circumferential direction position of the penetration, $\theta_{inclination}$ is the inclination angle that has been calculated in the first step, $\theta_{MIN}$ is a minimum value of an angle formed between the reactor pressure vessel and the penetration.

4. The method of an ultrasonic inspection according to claim 1, wherein the second step is to identify the circumferential direction position corresponding to the inclination angle, which has been calculated in the first step, based on the relationship between an inclination angle of the penetration and an circumferential direction position of the penetration, which have been calculated in advance.

5. The method of an ultrasonic inspection according to claim 1, wherein an image showing a cross section of the echo obtained from a result of an ultrasonic inspection performed on the penetration by the ultrasonic inspection apparatus and an image showing a cross section of the structure of the penetration to be inspected are combined and displayed on the display unit, the cross section of the structure of the penetration at the circumferential direction position that has been identified being present on the cross section of the echo.

6. The method of an ultrasonic inspection according to claim 5, the method further comprising the steps of:

matching a scanning surface shown in the image showing the cross section of the echo with the position of a surface shown in the image showing the cross section of the structure of the penetration;

calculating a distance between the center of the ultrasonic wave and the end of the inner diameter of the penetration to be inspected to obtain a position of transmission of an ultrasonic wave on the cross section of the structure; and matching the position of a transmission point of the echo on the cross section of the structure with the position of the transmission of the ultrasonic wave on the cross section of the structure for image combining.

7. The method of an ultrasonic inspection according to claim 6, the method further comprising the steps of:

calculating a distance between the center of the ultrasonic probe and the end of the inner diameter of a penetration adjacent to the penetration to be inspected;

subtracting the calculated distance from a distance between the penetration to be inspected and the adjacent penetration to calculate a distance between the penetration to be inspected and the ultrasonic probe; and obtaining a position of transmission of an ultrasonic wave on the cross section of the structure.

8. The method of an ultrasonic inspection according to claim 6, the method further comprising the steps of:

measuring a propagation distance of an echo transmitted from the penetration to be inspected or from the adjacent penetration;

calculating a distance between the penetration to be inspected and the ultrasonic probe based on the propagation distance; and obtaining a position at which an ultrasonic wave is transmitted on the cross section of the structure.

9. An apparatus for an ultrasonic inspection of a reactor pressure vessel, the apparatus comprising:

an ultrasonic inspection device;

a scanning mechanism for causing an ultrasonic probe of the ultrasonic inspection apparatus to scan the outer surface of the reactor pressure vessel that is present between penetrations; and means for measuring an inclination angle of at least one of the penetrations relative to a wall surface of the reactor pressure vessel based on a result of transmission and reception of an ultrasonic wave by use of the ultrasonic probe.

10. The apparatus for an ultrasonic inspection of a reactor pressure vessel according to claim 9, further comprising:

means for calculating a circumferential direction position of a penetration that is to be inspected by using an ultrasonic wave based on the inclination angle.

* * * * *